United States Patent
Perrine et al.

(10) Patent No.: US 10,111,846 B2
(45) Date of Patent: *Oct. 30, 2018

(54) S ISOMERS OF ALPHA-METHYL-HYDROCINNAMIC ACID FOR THE TREATMENT OF BLOOD DISORDERS

(71) Applicants: Susan Park Perrine, Weston, MA (US); Douglas V. Faller, Weston, MA (US)

(72) Inventors: Susan Park Perrine, Weston, MA (US); Douglas V. Faller, Weston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,175

(22) Filed: Feb. 9, 2017

(65) Prior Publication Data
US 2017/0312235 A1 Nov. 2, 2017

Related U.S. Application Data

(63) Continuation of application No. 14/868,638, filed on Sep. 29, 2015, now Pat. No. 9,603,818, which is a continuation of application No. 13/508,236, filed as application No. PCT/US2010/055455 on Nov. 4, 2010, now Pat. No. 9,173,860.

(60) Provisional application No. 61/258,108, filed on Nov. 4, 2009.

(51) Int. Cl.
| | |
|---|---|
| *A61K 31/192* | (2006.01) |
| *A61K 9/00* | (2006.01) |
| *A61K 9/08* | (2006.01) |
| *A61K 31/16* | (2006.01) |
| *A61K 31/165* | (2006.01) |
| *A61K 31/24* | (2006.01) |

(52) U.S. Cl.
CPC .......... *A61K 31/192* (2013.01); *A61K 9/0053* (2013.01); *A61K 9/0095* (2013.01); *A61K 9/08* (2013.01); *A61K 31/16* (2013.01); *A61K 31/165* (2013.01); *A61K 31/24* (2013.01)

(58) Field of Classification Search
None
See application file for complete search history.

(56) References Cited

U.S. PATENT DOCUMENTS

| | | | |
|---|---|---|---|
| 5,216,019 A | 6/1993 | Kamprad | |
| 6,133,645 A | 10/2000 | Grimmett | |
| 6,451,334 B2 | 9/2002 | Perrine | |
| 2001/0027215 A1 | 10/2001 | Perrine | |
| 2009/0082444 A1 | 3/2009 | Perrine | |

OTHER PUBLICATIONS

Burns et al., "Butyrate induces selective transcriptional activation of a hypomethylated embryonic globin gene in adult erythroid cells", Blood 72(5) 1536-1542 (1988).
Charache et al., "Treatment of sickle cell anemia with 5-azacytidine results in increased fetal hemoglobin production and is associated with nonrandom hypomethylation of DNA around the gamma-delta-beta-globin gene complex" Proc Natl Acad Sci USA 80(15) 4842-4846 (1983).
Charache et al., "Hydroxyurea-induced augmentation of fetal hemoglobin production in patients with sickle cell anemia", Blood 69(1) 109-116 (1987).
Ginder et al., "Activation of a chicken embryonic globin gene in adult erythroid cells by 5-azacytidine and sodium butyrate", Proc Natl Acad Sci USA 81(13) 3954-3958 (1984).
Letvin et al., "Augmentation of fetal-hemoglobin production in anemic monkeys by hydroxyurea", N Engl J Med 310 (14) 869-873 (1984).

(Continued)

*Primary Examiner* — Kortney L. Klinkel
*Assistant Examiner* — Tori Strong
(74) *Attorney, Agent, or Firm* — Nixon Peabody LLP

(57) ABSTRACT

The present intervention generally relates to compositions comprising S-isomer of alpha-methyl-hydrocinnamic acid for the treatment and/or prevention of blood disorders and blood deficiencies, as well as methods for treating blood disorders and/or blood deficiency in a subject by administering a composition comprising S-isomer of alpha-methyl-hydrocinnamic acid to the subject to ameliorate at least one symptom associated with the blood disorder. Another aspect relates to administration of an S-isomer of alpha-methyl-hydrocinnamic acid stimulate multi-lineage hematopoietic cell production in a subject, for example, increasing the numbers of circulating neutrophils, erythrocytes and platelets. Accordingly, one aspect of the present invention relates to administration of S-isomer of alpha-methyl-hydrocinnamic acid, e.g., by oral administration to a subject for the treatment of blood disorders, for example but not limited to, hemaglobinapathy, thalassemia and aplastic anemia. In some embodiments, the oral pharmaceutical formulation comprising an S-isomer of α-methyl-hydrocinnamic acid can be used to increase red blood cell proliferation, or increase the proliferation of hemoglobin-expressing cells in a subject in need thereof, e.g., a subject having a blood deficiency such as a subject undergone chemotherapy or radiation exposure or radiation therapy. In some embodiments, a formulation comprising an S-isomer of alpha-methyl-hydrocinnamic acid (ST7S) can be used to simulate myelopiesis or erythropoiesis in a subject in need thereof.

16 Claims, 14 Drawing Sheets

(56) References Cited

OTHER PUBLICATIONS

Nudel et al., "Differential effects of chemical inducers on expression of beta globin genes in murine erythroleukemia cells", Proc Natl Acad Sci USA 74(3) 1100-1104 (1977).

Oliva et al., "Histone hyperacetylation can induce unfolding of the nucleosome core particle", Nucleic Acids Res 18(9) 2739-2747 (1990).

Partington et al., "Human globin gene transcription in injected Xenopus oocytes: enhancement by sodium butyrate" EMBO J 3(12) 2787-2792 (1984).

Perrine et al., "Butryic acid analogues augment gamma globin gene expression in neonatal erythroid progenitors", Biochem Biophys Res Commun 148(2) 694-700 (1987).

Takahashi et al., "Differentiation of cultured Friend leukemia cells induced by short-chain fatty acids" Gan 66(5) 577-580 (1975).

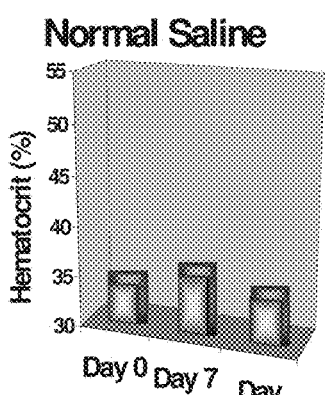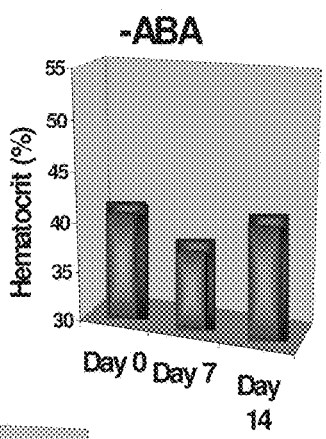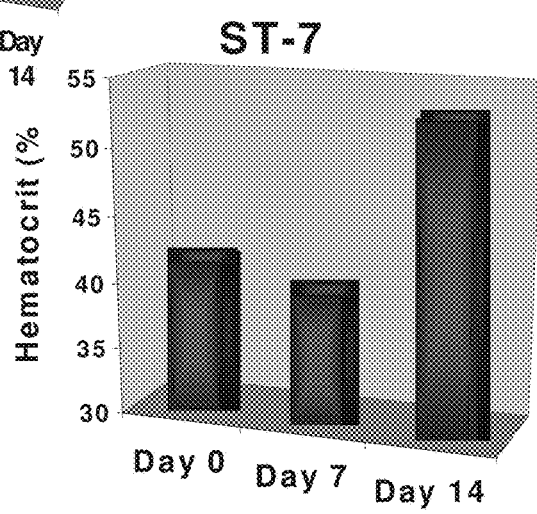

Normal mouse

Irradiated Mouse: Untreated Control

Irradiated Mouse ST7 Treatment

S ISOMERS OF ALPHA-METHYL-HYDROCINNAMIC ACID FOR THE TREATMENT OF BLOOD DISORDERS

CROSS REFERENCE TO RELATED APPLICATIONS

This application is a Continuation Application of U.S. patent application Ser. No. 14/868,638 filed Sep. 29, 2015, which is a Continuation Application which claims priority to U.S. patent application Ser. No. 13/508,236 filed Jul. 30, 2012, now U.S. Pat. No. 9,173,860, issued Nov. 3, 2015, which is a 35 U.S.C. § 371 National Phase Application of International Application No. PCT/US2010/055455 filed Nov. 4, 2010, which designates the U.S., and which claims benefit under 35 U.S.C. 119(e) of U.S. Provisional Application Ser. No. 61/258,108 filed on Nov. 4, 2009, the contents of which are incorporated herein by reference in their entirety.

GOVERNMENT SUPPORT

This invention was made with government support under Contract No. DK52962 awarded by the National Institutes of Health. The Government has certain rights in this invention.

FIELD OF THE INVENTION

The present invention is directed to methods and compositions for the treatment of blood disorders and increase in hematopoietic cells following radiation and chemotherapy treatment in a subject, the methods and compositions comprising S isomer of α-methyl-hydrocinnamic acid.

BACKGROUND OF THE INVENTION

Hematopoiesis, or the formation of blood cells, begins in the developing human embryo as clusters of stem cells. Although the spleen, lymph nodes and bone marrow all make small contributions to blood cell development, not until the fourth month does the bone marrow become the principal site of hematopoiesis.

In the adult, hematopoiesis involves the bone marrow, the lymph nodes and the spleen. These organs and associated tissues are traditionally divided into myeloid and lymphoid tissue-types. The myeloid/lymphoid division is somewhat artificial as these two types of tissues are believed to originate from a single pluripotent stem cell.

Lymphoid and myeloid stem cells, formed from division of the pluripotent cell, are precursors for all subsequent cell types. The bone marrow provides a unique environment for pluripotent and committed cells.

Hemoglobin comprises four protein chains, two alpha chains and two beta chains ($\alpha_2 \beta_2$), interwoven together, each with its own molecule of iron and with a combined molecular weight of about 68 kD. The hemoglobin macromolecule is normally glycosylated and upon absorbing oxygen from the lungs transforms into oxyhemoglobin ($HbO_2$). There are at least six distinct forms of hemoglobin, each expressed at various times during development. Hemoglobin in the embryo is found in at least three forms, Hb-Gower 1 ($\zeta_2\epsilon_2$), Hb-Gower 2 ($\alpha_2\epsilon_2$), and Hb-Portand $\zeta_2\gamma_2$). Hemoglobin in the fetus comprises nearly totally HbF ($\alpha_2\gamma_2$), whereas hemoglobin in the adult contains about 96% HbA ($\alpha_2 \beta_2$), about 3% $HbA_2$ ($\alpha_2 \delta_2$) and about 1% fetal HbF ($\alpha_2\gamma_2$). The embryonic switch of globin expression from $\zeta$ to $\alpha$ and from $\epsilon$ to $\gamma$ begins in the yolk sac. However, chains of embryonic $\zeta$ and $\epsilon$ have been found in the fetal liver and complete transition to the fetal form does not occur until late in fetal development. The fetal switch from $\gamma$ to $\beta$ begins later in erythropoiesis with the amount of $\gamma$ globin produced increasing throughout gestation. At birth, $\beta$ globin accounts for about 40% of non-$\alpha$ globin chain synthesis and thereafter continues to rapidly increase. Neither the switch from embryonic to fetal or fetal to adult appears to be controlled through cell surface or known cytokine interactions. Control seems to reside in a developmental clock with the switch occurring at times determined only by the stage of fetal development.

Defects or mutations in globin chain expression are common. Some of these genetic mutations pose no adverse or only minor consequences to the person, however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions.

Individuals with severe sickle cell anemia develop no symptoms until about five to six months after birth. In these infants it was determined that fetal hemoglobin did not interact with HbS and, as long as sufficient quantities were present, could modulate the effects of HbS disease. This modulating effect of $\beta$ globin is also observed with other $\beta$ globin disorders, such as HbC and HbD, and other mutations of the $\beta$ chain. HbS polymerization is also significantly affected by the hemoglobin concentration of the cell. The higher the HbS concentration, the greater the chances for contact between two or more HbS molecules. Dehydration increases hemoglobin concentration and greatly facilitates sickling.

The thalassemia syndromes are a heterogenous group of disorders all characterized by a lack of or a decreased synthesis of the globin chains of HbA. Deficiencies of $\beta$-globin expression are referred to as $\beta$-thalassemias and deficiencies of $\alpha$-globin, $\alpha$-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of $\alpha$ or $\beta$ globin protein.

A variety of small molecules have been shown to effect hemoglobin or fetal globin expression. Early experiments demonstrated that acetate ($CH_3COOH$), propionate ($CH_3CH_2COOH$), butyrate ($CH_3CH_2CH_2COOH$) and isobutyrate ($CH_3CH(CH_3)COOH$) all induced hemoglobin synthesis in cultured Friend leukemia cells (E. Takahashi et al., Gann 66:577-80, 1977). Additional studies showed that polar compounds, such as acid amides, and fatty acids could stimulate the expression of both fetal and adult globin genes in murine erythroleukemia cells (U. Nudel et al., Proc. Natl. Acad. Sci. USA 74:1100-4, 1977). Hydroxyurea ($H_2NCONHOH$), another relatively small molecule, was found to stimulate globin expression (N. L. Letvin et al., N. Engl. J. Med. 310:869-73, 1984). Stimulation, however, did not appear to be very specific to fetal globin (S. Charache et al., Blood 69:109-16, 1987). Hydroxyurea is also a well-known carcinogen making its widespread and long term use as a pharmaceutical impractical.

One of the major breakthroughs in the treatment of hemoglobinopathies was made when it was discovered that butyric acid (butanoic acid; $CH_3CH_2CH_2COOH$) accurately and specifically stimulated transcription of the human fetal ($\gamma$) globin gene (G. A. Partington et al., EMBO J. 3:2787-92, 1984). These findings were quickly confirmed in vivo wherein it was shown that pharmacological doses of butyric acid greatly increased expression of fetal globin in adult chickens rendered anemic by injections with phenylhydrazine (G. D. Ginder et al., Proc. Natl. Acad. Sci. USA 81:3954-58, 1984). Selective transcriptional activation was again thought to be due to hypo-methylation of the embryonic gene (L. J. Burns et al., Blood 72:1536-42, 1988). Others speculated that histone acetylation, a known effect of butyric acid, may be at least partly responsible for increased fetal gene expression (L. J. Burns et al., EMBO J. 3:2787, 1984).

Over 50 derivatives of butyric acid have since been found to be effective in stimulating fetal globin production (S. P. Perrine et al., Biochem. Biophys. Res. Commun. 148:694-700, 1987). Some of these include butyric acid salts such as sodium and arginine butyrate, $\alpha$-amino-n-butyric acid (butyramide; $CH_3CH_2CH_2CONH_2$), and isobutyramide ($CH_3CH(CH_3)CONH_2$). Although promising in pilot clinical studies, treated patients were unable to maintain adequate levels of fetal globin in their system. It was later determined that many of these forms of butyric acid had extremely short-half lives. Oxidation in the serum, clearance by hepatocytes and filtration through the kidneys rapidly eliminated these agents from the patient's system. With others, patients rapidly developed tolerance or metabolites of compounds had the opposite desired effect.

Several studies have focused on the mechanism whereby butyric acid and other small organic molecules have been able to stimulate fetal globin expression (R. Oliva et al., Nuc. Acids Res. 18:2739, 1990). Experiments with cells in culture have indicated that butyric acid may act by increasing the level of histone acetylation by, possibly, decreasing the activity of one or more histone deacetylase. Resulting histone hyperacetylation may produce nucleosome unfolding and thereby increased gene expression. Other studies have indicated that hypo-methylation of the area of DNA around the $\beta$ gene complex correlates with increased $\gamma$ globin gene expression in thalassemic patients (S. Charache et al., Proc. Natl. Acad. Sci. USA 80:4842-46, 1983). Alternatively, butyric acid and other small molecules may function to increase specific gene expression by acting directly on agents which regulate transcription, the so-called transcription factors. These factors bind to sequence-specific sites along the genome at areas which control the expression of proximally located genes.

The present invention is directed toward overcoming one or more of the problems discussed above.

SUMMARY OF THE INVENTION

In one aspect, the invention is directed to an oral pharmaceutical formulation comprising: (i) a pharmaceutically effective amount of an S isomer of $\alpha$-methyl-hydrocinnamic acid (ST7S), or a pharmaceutically acceptable salt thereof; and (ii) a pharmaceutically acceptable carrier or diluent, wherein the oral pharmaceutical formulation is in solution or a dry solid. In another embodiment of a formulation or method according to the invention, the alpha-methyl-hydrocinnamic acid is the R isomer.

In additional separate embodiments of a formulation of the invention, the formulation is in solution as a dispersion, mixture, liquid, spray, or capsule; or is a dry solid as a powder, pill, tablet, or capsule. In another embodiment, the formulation further comprises a flavoring agent.

In another aspect, the invention is directed to a method for treating a blood disorder in a subject comprising administering to the subject an oral pharmaceutical composition comprising: (i) a pharmaceutically effective amount of an S isomer of $\alpha$-methyl-hydrocinnamic acid, or a pharmaceutically acceptable salt thereof; and (ii) a pharmaceutically acceptable carrier or diluent, wherein the oral pharmaceutical composition is in solution or a dry solid, and wherein the oral pharmaceutical composition is administered to the subject by oral administration, thereby treating the blood disorder in the subject. The method may, in additional separate embodiments, further comprise monitoring hemoglobin-expressing cells to ensure that cell proliferation is stimulated, and that cell viability is not significantly decreased; and/or further comprise obtaining the S isomer of $\alpha$-methyl-hydrocinnamic acid.

In another embodiment of a method of the invention, the composition is in solution as a dispersion, mixture, liquid, spray, or capsule. In yet another embodiment of a method of the invention, the composition is a dry solid as a powder, pill, tablet, or capsule. In still another embodiment of a method of the invention, the composition further comprises a flavoring agent.

In another embodiment of a method of the invention, the blood disorder is a hemoglobinopathy or a thalassemia.

In another aspect, the invention is directed to a method for stimulating myelopoiesis and/or erythropoiesis in a subject, comprising administering to the subject an oral pharmaceutical composition comprising: (i) a pharmaceutically effective amount of an S isomer of $\alpha$-methyl-hydrocinnamic acid, or a pharmaceutically acceptable salt thereof; and (ii) a pharmaceutically acceptable carrier or diluent, wherein the oral pharmaceutical composition is in solution or a dry solid, and wherein the oral pharmaceutical composition is administered to the subject by oral administration, thereby stimulating myelopoiesis and/or erythropoiesis in the subject.

In another embodiment, the method of the invention further comprises obtaining the S isomer of $\alpha$-methyl-hydrocinnamic acid. In another embodiment of a method of the invention, the composition is in solution as a dispersion, mixture, liquid, spray, or capsule. In yet another embodiment of a method of the invention, the composition is a dry solid as a powder, pill, tablet, or capsule. In still another embodiment of a method of the invention, the composition further comprises a flavoring agent.

In another embodiment, the method of the invention is used to treat a blood disorder. In still another embodiment, the blood disorder is caused by radiation therapy or chemotherapy. The blood disorder may, in yet another embodiment, be aplastic anemia.

BRIEF DESCRIPTION OF THE DRAWINGS

FIGS. 1A-1D show that ST7 Stimulates Erythropoesis. FIG. 1A-1C shows ST7 once daily to mice for 5 days: Then: ST7 induced a significant increase in hematocrit by day 14. FIG. 1D shows Oral ST7 in Baboon 497. Daily phlebotomy, chronic anemia ST-7 (50 mg/kg per day for 5 days a week over 3 weeks. Resulted in an increase in total hemoglobin level (2.5 g/dL). There was an absolute increase in hematocrit level of 7 percentage points (28% of baseline).

FIG. 2A shows oral administration of ST7 to a baboon results in a 3-fold stimulation of WBC count over 6 days. FIG. 2B shows the effects of hemokines on CFU-GEM colony formation. FIG. 2B is the CFU-GEM growth from human hematopoietic cultures treated with ST7 and other SCFD derivatives (AB is arginine butyrate, ST38 is 3-(3,4 dimethyloxyphenyl) propionic acid; PAA is phenoxyacetic acid, ST20 is 2,2 dimethyl butyrate and ST35 is 4-Methoxycinnamic acid, and shows that ST7 increases CFU-GM Colony formation.

FIG. 3A shows absolute neutrophil counts (ANC) (K/µ4) over long term (47 days) for baboon GG24 with administration of ST7S at 1-5 days and 34-38 days. FIG. 3B shows ANC counts (K/µ4) over long term (47 days) for baboon FM45 with ST7S administration at 1-5 days and 35-38 days. FIG. 3C shows absolute neutrophil counts (ANC) in Baboon GG24 with short (3 day) administration of ST7S (100 mg/kg) administered at day 0-2 and day 7-9).

FIG. 4A shows IV administration of ST7 to 3 baboons on days 1-3 and 7-9 results in a stimulation of platelet count in all animals. FIG. 4B shows a 3-fold rise in platelet counts detected in a Baboon (08505) treated with ST7S.

FIG. 5A shows the NE (K/µL) for saline control treated mice. FIG. 5B shows the NE (K/µL) for ST7 treated mice. FIG. 5C shows the NE (K/µL) for G-CSF treated mice. ST7 treatment accelerated recovery of ANC by day 13 as efficiently as G-CSF.

FIG. 7A is a histogram showing hemokines SCFADs induce anti-apoptotic proteins. FIG. 7B is a western blot of Mcl-$1_L$ to Mcl-$1_S$ protein expression (with β-actin as a protein loading control). Ratios of Mcl-$1_L$ to Mcl-$1_S$ are shifted towards anti-apoptotic actions after exposure to ST7. FIG. 7C shows human neutrophil survival in vitro with or without hemokines ST7 (200 µM), ST7 (50 µM), RB3 and G-CSF. ST7 suppresses apoptosis in cultured normal human neutophils.

FIG. 8A shows bioavailability after ST7 is administered orally (shown by the blue dotted line) or IV (red solid line). Administration orally or via IV results in nearly identical PK profiles in non-human primates, demonstrating that >90% oral bioavailability of ST7. Target does equivalent to 20 mg/kg in an adult human. FIG. 8B shows ST7 administered orally to a normal human subject at 1 or 1.4 grams. Drug levels of ST7 persist above the target dose for several hours after administration.

FIG. 9 is a graph of absolute neutrophil count (ANC) response to NaST7 (500 mg/kg IP and 300 mg/kg IP) after sub-lethal does of irradiation where mice were exposed to 6 Gy irradiation on day 0 and daily ST7 (enantiomer) was administered at two doses, beginning day 1. Control (Saline) animals had an ANC<200 for 7 days (e.g., between days 3-10), whereas ST7 prevented ANC decline below 200 cells/mm$^2$ at any time.

FIG. 10A shows an image of histology of bone marrow in a normal (non-irradiated) healthy mouse. FIG. 10B shows a histology image of the bone marrow in a lethal-irradiated untreated mouse showing hypocellular Marrow. FIG. 10C shows a histology image of the bone marrow in a lethal-irradiated mouse treated with ST7S showing normocellular marrows in ST-7S-treated animals, with neutrophil differentiation. Mice were irradiated at LD90 on day 0, and received daily SC injections of ST7-S or saline (control) starting Day 1. Bone marrow was examined on Day 15.

FIG. 12 is a graph showing increase in both white blood cells (WBC) and Absolute neutrophil counts (ANC) after oral administration of 200 mg/kg ST7S on days 0-4 results in a 3-fold stimulation in WBC and neutrophil counts over 6 days.

FIG. 13A is a graph showing that sodium α-methyl hydrocinnamate is almost insoluble in aqueous solution at pH values of 7 and below, and has a saturation solubility in water is 655 mg/ml. FIG. 13B is graph showing the pH stability profile for Sodium α-Methyl Hydrocinnamate

DETAILED DESCRIPTION OF THE INVENTION

Figure 1D:
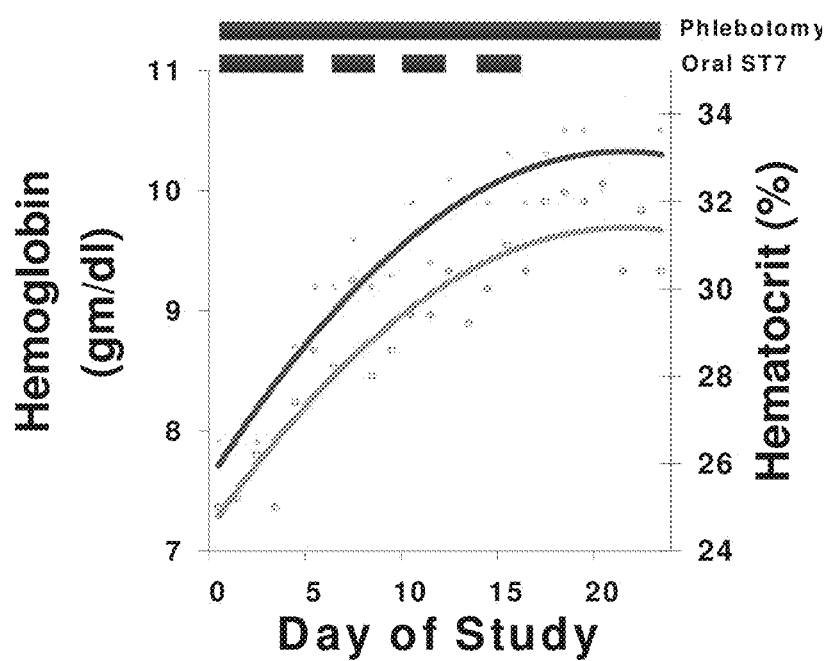

The present invention generally relates to an oral pharmaceutical formulation comprising an S-isomer of alpha-methyl-hydrocinnamic acid (herein referred to as "ST7S") and pharmaceutically acceptable salts thereof. Herein, it is demonstrated that administration of ST7S, e.g., oral administration, can stimulate multi-lineage hematopoietic cell production in a subject, for example, increasing the numbers of circulating neutrophils, erythrocytes and platelets. Accordingly, in some embodiments, the composition can be administered by any means, e.g., orally, to a subject for the treatment of blood disorders, for example but not limited to, hemaglobinapathy, thalassemia and aplastic anemia. In some embodiments, the oral pharmaceutical formulation comprising an S-isomer of alpha-methyl-hydrocinnamic acid (ST7S) can be used to increase red blood cell proliferation, or increase the proliferation of hemoglobin-expressing cells. In some embodiments, a formulation comprising an S-isomer of alpha-methyl-hydrocinnamic acid (ST7S) can be used to simulate myelopiesis or erythropoiesis in a subject.

In particular, herein the inventors have demonstrated that ST7, e.g., ST7S is a multi-lineage oral hematapoetic stimulant. Herein it is demonstrated that ST7, e.g., ST7S stimulates all hematopoietic lineages, for example, neutrophils, and is useful for administering to subjects, e.g., human subjects who are recovering from transplants, radiation treatment and others conditions where it is desirable to increase hematopoietic lineages, for example, administering to a donor subject in the place of, or with G-CSF, prior to bone marrow donation or hematapoeitic stem cell donation.

In some embodiments, ST7, e.g., ST7S can be administered orally, as an oral agent. In some embodiments, an oral composition comprising ST7, e.g., ST7S can be administered to a subject in need (e.g., a subject with low platelet count, or a subject where it is desirable to increase platelet count) at frequent intervals, for example but not limited at least once/day. In some embodiments, other administration regimens can be used, for example at least 2, or more-times a day, or at least about 2-times a week, or at least about once a week, or at least about every other day, or at least about every other week and the like. Herein the inventors demonstrate that ST7, e.g., ST7S accelerates neutrophil recovery following radiation in an in vivo animal model, and increases all hematopoietic lineages in non-human primates, e.g., baboons, and increases the number of neutrophils, platelets, and cells which express hemaglobin (Hgb).

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "hematopoietic cell" as used herein is a collective term for all bone marrow-derived cell types in the blood (see also: hematopoiesis). Thus, a hematapoeitic cell refers to mature cell types and their immature precursors that are identifiable either by morphology or, mostly, by a distinct pattern of cell surface markers. The term is used to distinguish these cells from other cell types found in the body and also includes T-cells and distinctive subsets, which are the only hematopoietic cells that are not generated in the bone marrow. The specific precursors of mature blood cells that are defined by their ability to reconstitute completely bone marrow functions after its destruction are hematopoietic stem cells. Hematopoietic cells are subgrouped broadly into myeloid cells (erythrocytes, thrombocytes, neutrophils, monocytes and macrophages, eosinophils, basophils, mast cells) and the lymphoid cells (B-cells, various types of T-cells, NK-cells). Those cells that do not produce hemoglobin are leukocytes. Those cells that produce hemoglobin (red blood cells) are erythrocytes. A collective term for cells engaged in immune responses is lymphocytes.

The term "myelopiesis" as used herein refers to the formation of myeloid cells, including eosinophilic granulocytes, basophilic granulocytes, neutrophilic granulocytes, and monocytes. In hematology, myelopoiesis is the production of blood cells in the bone marrow. Without wishing to be bound by theory, a myeloid progenitor can differentiate in the bone marrow into granulocytes, macrophages (mature monocytes), mast cells (whose blood-borne progenitor is not well defined), and dendritic cells of the innate immune system. The granulocytes, also called polymorphonuclear leukocytes because of their oddly shaped nuclei, give rise to three short lived cell types including eosinophils, basophils, and neutrophils. A granulocyte differentiates into a distinct cell type by a process called granulopoiesis. In this process it first transforms from a common myeloblast (myeloid progenitor) to a common promyelocyte. This promyelocyte gives rise to a unique myelocyte that for the first time can be classified as an eosinophil, basophil, or neutrophil progenitor based on the histological staining affinity (eosinophilic, basophilic, or neutral granules). The unique myelocyte next differentiates into a metamyelocyte and then a band cell, with a "C" shaped nucleus, before becoming a mature eosinophil, basophil, or neutrophil. Macrophages come from monoblast progenitors that differentiate into promonocytes, which mature into monocytes. Monocytes eventually enter the tissues and become macrophages. The term myelopiesis includes the process of Granulopoiesis (Myeloblast, Promyelocyte, Myelocyte, Metamyelocyte, Band cell production); Monocytopoiesis (production of Monoblast, Promonocyte); MEP Thrombopoiesis (production of Megakaryoblast, Promegakaryocyte); Erythropoiesis (production of Proerythroblast, Normoblast, Reticulocytes).

The term "haematopoiesis" (also referred to herein ashaemopoiesis or hemopoiesis) refers to the formation of blood cellular components, and includes both the process of myleposieis and general extramedullary hematopoiesis. Without wishing to be bound by theory, all cellular blood components are derived from hematopoietic stem cells. In a healthy adult person, approximately $10^{11}$-$10^{12}$ new blood cells are produced daily in order to maintain steady state levels in the peripheral circulation.

The term "erythropoiesis" as used herein refers the process by which red blood cells (erythrocytes) are produced. Without wishing to be bound by theory, Erythropoiesis is stimulated by decreased $O_2$ delivery to the kidneys, which then secrete the hormone erythropoietin, which activates increased erythropoiesis in the hemopoietic tissues. In mammals (including humans), erythropoiesis usually occurs within the red bone marrow. In the early fetus, erythropoiesis takes place in the mesodermal cells of the yolk sac. By the third or fourth month, erythropoiesis moves to the spleen and liver. After seven months, erythropoiesis occurs in the bone marrow. However, in humans with certain diseases and in some animals, erythropoiesis also occurs outside the bone marrow, within the spleen or liver, which is referred to as extramedullary erythropoiesis.

The term "hematopoietic stem cell" or "HSC" as used herein refers to a multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). The term "hematopoietic stem cells" can also refer to stem cells or progenitor cells found in bone marrow and peripheral blood that are greater than about 10 µm in diameter and are capable of differentiating into any of the specific types of hematopoietic or blood cells, such as erythrocytes, lymphocytes, macrophages and megakaryocytes. HSCs are reactive with certain monoclonal antibodies which are now recognized as being specific for hematopoietic cells, for example, CD34+/CD45+. The term "hematopoietic stem cells" also refers to as "HSCs" refers to all types of hematopoietic cells throughout their differentiation from self-renewing hematopoietic stem cells through immature precursor cells of the various blood lineages to and including the mature functioning blood cells as would be understood by persons skilled in the art. Hematopoietic stem cells (HSCs) are multipotent stem cells that give rise to all the blood cells including myeloid and lymphoid lineages. These HSCs are responsible for constant maintenance and immune protection of every cell type of the body. Basically there are two types of HSC's, short term and long term stem cells. A short term HSC has limited hematopoietic capabilities whereas a true HSC's are the one which can self-renew itself for the entire life span. But it is very difficult to distinguish between short term and long term HSCs. As HSC's look and behave in culture like ordinary white blood cells, it's also difficult to identify them by morphology (size and shape). The only way to identify them is through cell surface proteins. Human HSC that express high levels of CD34 and low or absent levels of CD33, CD38, thy-1, and CD71, appear to be enriched for primitive progenitor and HSC activity, while more mature progenitors express one or more of these markers. Stem cells can also be identified based on side population depending on the surface markers used for staining. HSC are useful for hematopoietic stem cell transplantation, which involves administration, e.g., intravenous infusion of autologous or allogenic stem cells collected from bone marrow, peripheral blood or umbilical cord blood to reestablish hematopoietic function in patients with damaged or defective bone marrow or immune system.

The term "proliferation" or "proliferating" as used herein refers to an increase in a number of cells in a population of cells by means of cell division or cell renewal. Cell proliferation, e.g., neutrophil proliferation as disclosed herein is generally understood to result from the coordinated activation of multiple signal transduction pathways in response to the environment, and can result in a direct replication of neutrophils or increase in hematopoietic cell which produce neutrophil cells.

The term "isomer" as used herein refers to a compound with the same molecular formula but different structural formulas. Isomers do not necessarily share similar properties, unless they also have the same functional groups. There are many different classes of isomers, like stereoisomers, enantiomers, geometrical isomers, etc. There are two main forms of isomerism: structural isomerism and stereoisomerism (spatial isomerism).

The term "S isomer" as used herein refers to an enantiomer with the chiral center S according to a system by which its substituents are each assigned a priority, according to the Cahn-Ingold-Prelog priority rules (CIP), based on atomic number, where the priority of atomic number decreases in counterclockwise direction, it is S enantiomer (from the Latin Sinestra, meaning "left"). Without wishing to be limited to theory, if the center is oriented so that the lowest-priority of the four is pointed away from a viewer, the viewer will then see two possibilities: If the priority of the remaining three substituents decreases in clockwise direction, it is labeled R (from the Latin Rectus, meaning "right"), if it decreases in counterclockwise direction, it is S (from the Latin Sinestra, meaning "left").

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

Thus, as used herein, the term "pharmaceutically acceptable salt," is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets.

As used herein, a "prodrug" refers to compounds that can be converted via some chemical or physiological process (e.g., enzymatic processes and metabolic hydrolysis) to either S-α-methyl-hydrocinnamic acid or R-α-methyl-hydrocinnamic acid. A prodrug may be inactive when administered to a subject, i.e. an ester, but is converted in vivo to an active compound (e.g. S-α-methyl-hydrocinnamic acid or R-α-methyl-hydrocinnamic acid), for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11, 345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "*Prodrugs*", *Br. J. Clin. Pharmac.* 28: 497-507 (1989), content of all of which is herein incorporated by reference in its entirety.

The term "subject" as used herein refers to a vertebrate, preferably a mammal, more preferably a primate, still more preferably a human. Mammals include, without limitation, humans, primates, wild animals, rodents, feral animals, farm animals, sports animals, and pets. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Mammals other than humans can be advantageously used as subjects that represent animal models of conditions or disorders associated blood disorders. In addition, the methods and compositions described herein can be used to treat domesticated animals and/or pets.

A subject can be one who has been previously diagnosed with or identified as suffering from or having a blood disorder.

A subject can one who is currently being treated for a blood disorder.

In some embodiments of the aspects described herein, the method further comprising diagnosing a subject for a blood disorder before onset of treatment with a method described herein. Methods of diagnosing blood disorders are well known in the art.

In some embodiments, the method further comprising selecting a subject diagnosed with a blood disorder before onset of treatment with a method described herein.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) reduce or inhibit the growth of transformed (cancer) cells in a relevant in vitro assay or cause a measurable improvement in an animal model of cancer and/or (ii) induce expression of fetal hemoglobin in a relevant in vitro assay or cause a measurable improvement in an animal model of a hemoglobinopathy and/or thalassemia, for example, a sickle cell disease. Alternatively, a "therapeutically effective amount" is an amount of a compound of this invention sufficient to confer a therapeutic or prophylactic effect on the treated subject against (i) cancer and/or (ii) a hemoglobinopathy and/or thalassemia. Therapeutically effective amounts will vary, as recognized by those skilled in the art, depending on the specific disease treated, the route of administration, the excipient selected, and the possibility of combination therapy.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy.

Physiological effects that can be measured to determine the therapeutically effective amount include, without limitation, substrate protein hyperacetylation (histone, tubulin, hsp90, p53, STAT, etc.), gene induction (fetal hemoglobin, spinal muscle atrophy gene), impaired protein trafficking, improved neuronal vesicle trafficking, induction of apoptosis, cell cycle arrest, and induction of p21.

Relevant assays to measure such effects include, without limitation, Western (immuno)blot, RT-PCR, expression profile by microarray or other technology, high-content immunofluorescence, cytoblot, biochemical inhibition of HDAC proteins, alterations in chromatin structure by ChIP, and alterations in histone and/or other target protein modification by mass spectrometry.

The term "obtaining" as in "obtaining the compound" is intended to include purchasing, synthesizing or otherwise acquiring the compound (or indicated substance or material).

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

In General:

The present invention generally relates to an oral pharmaceutical formulation comprising an S-isomer of alpha-methyl-hydrocinnamic acid (herein also referred to as "ST7S") and is commonly also referred to in the art as 1-methyl-2-phenylpropionic acid, and pharmaceutically acceptable salts thereof.

S-isomer of alpha-methyl-hydrocinnamic acid has the following structure:

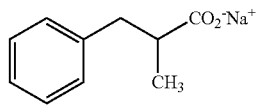

S-isomer of alpha-methyl-hydrocinnamic acid has the formula of $C_{10}H_{12}O_2$ (InChI is IS/C10H12O2/c1-8(10(11)12)7-9-5-3-2-4-6-9/h2-6,8H,7H2,1H3,(H,11,12)), and has a molecular weight of 164.204. In some embodiments, an S-isomer of alpha-methyl-hydrocinnamic acid can be a sodium salt, such as sodium α-methylhydrocinnamate, or sodium 2-methyl-3-phenylpropionate (formula of $C_{10}H_{11}NaO_2$).

S-isomer of Alpha-methyl-hydrocinnamic Acid

As disclosed herein, the composition comprises an S isomer of α-methyl-hydrocinnamic acid. A S isomer of α-methyl-hydrocinnamic acid can be formulated and prepared by method described, for example, in Fécourt, et al., Tetrahedron Asymmetry (2010), Alternatively, the S-α-methyl-hydrocinnamic acid can be prepared by resolving the racemic mixture of α-methyl-hydrocinnamic acid. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981).

As disclosed herein, the designations "R" and "S" are used to denote the absolute configuration of the α-methyl-hydrocinnamic acid about its chiral center. The designations may appear as a prefix or as a suffix; they may or may not be separated from the isomer by a hyphen; they may or may not be hyphenated; and they may or may not be surrounded by parentheses.

In some embodiments, the composition as disclosed herein for use in the methods as disclosed herein comprise a substantially pure composition of an S isomer of α-methyl-hydrocinnamic acid. In some embodiments, a composition comprising α-methyl-hydrocinnamic acid comprises at least about 80%, or at least about 85%, or at least about 90%, or at least about 92%, or at least about 95%, or at least about 97%, or at least about 98%, or at least about 99%, or at least about 99.5%, or at least about 99.8% or more than 99.8% of S isomer of α-methyl-hydrocinnamic acid. In some embodiments, a composition comprising α-methyl-hydrocinnamic acid for use in the methods as disclosed herein comprise less than 6% of R-isomer of α-methyl-hydrocinnamic acid, or less than about 5%, or less than about 4%, or less than about 3%, or less than about 2%, or less than about 1%, or less than about 0.5%, or less than about 0.2%, or less than about 0.1% of R-isomer of α-methyl-hydrocinnamic acid.

Salts of S-isomer of Alpha-methyl-hydrocinnamic Acid

The S-isomer of alpha-methyl-hydrocinnamic acid compounds of the invention that are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

Blood Disorders.

In one embodiment, the invention relates to compositions useful in the treatment and prevention of blood disorders such as anemia, thalassemia, and sickle cell disease. Compositions comprise proteins or chemicals that stimulate the specific expression of a globin protein or the proliferation or development of hemoglobin-expressing or other myeloid cells.

In another embodiment, the invention relates to methods and medical aids which utilize these compositions to treat blood disorders and/or to ameliorate symptoms associated with blood disorders.

Hemoglobinopathies and thalassemias can both be characterized as "blood disorders". Blood disorders include disorders that can be treated, prevented, or otherwise ameliorated by the administration of a compound of the invention. A blood disorder is any disorder of the blood and blood-forming organs. The term blood disorder includes nutritional anemias (e.g., iron deficiency anemia, sideropenic dysphasia, Plummer-Vinson syndrome, vitamin B12 deficiency anemia, vitamin B12 deficiency anemia due to intrinsic factor, pernicious anemia, folate deficiency anemia, and other nutritional anemias), myelodysplastic syndrome, bone marrow failure or anemia resulting from chemotherapy, radiation or other agents or therapies, hemolytic anemias (e.g., anemia due to enzyme disorders, anemia due to phosphate dehydrogenase (G6PD) deficiency, favism, anemia due to disorders of glutathione metabolism, anemia due to disorders of glycolytic enzymes, anemias due to disorders of nucleotide metabolism and anemias due to unspecified enzyme disorder), thalassemia, α-thalassemia, β-thalassemia, δβ-thalassemia, thalassemia trait, hereditary persistence of fetal hemoglobin (HPFP), and other thalassemias, sickle cell disorders (sickle cell anemia with crisis, sickle cell anemia without crisis, double heterozygous sickling disorders, sickle cell trait and other sickle cell disorders), hereditary hemolytic anemias (hereditary spherocytosis, hereditary elliptocytosis, other hemoglobinopathies and other specified hereditary hemolytic anemias, such as stomatocyclosis), acquired hemolytic anemia (e.g., drug-induced autoimmune hemolytic anemia, other autoimmune hemolytic anemias, such as warm autoimmune hemolytic anemia, drug-induced non-autoimmune hemolytic anemia, hemolytic-uremic syndrome, and other non-autoimmune hemolytic anemias, such as microangiopathic hemolytic anemia); aplastic anemias (e.g., acquired pure red cell aplasia (erythoblastopenia), other aplastic anemias, such as constitutional aplastic anemia and fanconi anemia, acute posthemorrhagic anemic, and anemias in chronic diseases), coagulation defects (e.g., disseminated intravascular coagulation (difibrination syndrome)), hereditary factor VIII deficiency (hemophilia A), hereditary factor IX deficiency (Christmas disease), and other coagulation defects such as Von Willebrand's disease, hereditary factor Xi deficiency (hemophilia C), purpura (e.g., qualitative platelet defects and Glanzmann's disease), neutropenia, agranulocytosis, functional disorders of polymorphonuclear neutrophils, other disorders of white blood cells (e.g., eosinophilia, leukocytosis, lymophocytosis, lymphopenia, monocytosis, and plasmacyclosis), diseases of the spleen, methemoglobinemia, other diseases of blood and blood forming organs (e.g., familial erythrocytosis, secondary polycythemia, essential thrombocytosis and basophilia), thrombocytopenia, infectious anemia, hypoproliferative or hypoplastic anemias, hemoglobin C, D and E disease, hemoglobin lepore disease, and HbH and HbS diseases, anemias due to blood loss, radiation therapy or chemotherapy, or thrombocytopenias and neutropenias due to radiation therapy or chemotherapy, sideroblastic anemias, myelophthisic anemias, antibody-mediated anemias, and certain diseases involving lymphoreticular tissue and reticulohistiocytic system (e.g., Langerhans' cell hystiocytosis, eosinophilic granuloma, Hand-Schuller-Christian disease, hemophagocytic lymphohistiocytosis, and infection-associated hemophagocytic syndrome).

In some embodiments, the blood deficiencies are acquired or genetic deficiencies. Genetic blood disorders are well known by persons of ordinary skill in the art, and include, without limitation, Thalassemias, Sickle cell disease, hereditary spherocytosis, G6PD Deficiency hemolytic anemia, Kostman's syndrome, Swachman-Diamond Syndrome, Cyclic neutropenia, Hereditary neutropenia, Dyskeratosis Congenita, Hereditary thrombocytopenia syndromes, Wiskott-Aldrich Syndrome, May-Hegglin anomaly, Thrombocytopenia with Absent Radii Syndrome, Fanconi's anemia and other hereditary blood disorders.

In some embodiments, the oral compositions of ST7S and methods as disclosed herein can be used for the treatment of neutropenia. Neutrophenia is a disorder of low white blood cell count in a subject, and is characterized by one or more of the following: an absolute neutrophil count (ANC) of less than 1500/microL. People suffering or diagnosed with neutrophia may result in hospitalization for treatment of fever, neutropenic sepsis, and can cause potentially fatal infection. Neutropenia is very common in subjects undergone or currently undergoing chemotherapy, transplants, radiation therapy and the like.

Current treatment for neutropenia are inadequate. Existing therapies include Granulocyte colony-stimulating factor (G-CSF, filgrastim) which, in 2008 US sales were about $929,201, Granulocyte-macrophage colony-stimulating factor (GM-CSF, sargramostim) which, in 2008 US sales were approximately $82,440, and Pegfilgrastim, a pegylated formulation of G-CSF, which in 2008 US sales were about $3,013,159.

Accordingly, the methods and oral composition comprising ST7S as disclosed herein can be used for the treatment of low platelet count, for example but not limited to, a low platelet count occurring in thrombocytopenia an/or platelet dysfunction. There is currently no or inadequate drug therapy, and the only current treatment is a platelet transfusion. In some embodiments, the methods and oral composition comprising ST7S as disclosed herein can be used for the treatment of low platelet count which is occurs as a consequence of other disorders, for example but not limited to, AIDS (acquired immunodeficiency syndrome); ITP (immune thrombocytopenic purpura); DIC (disseminated intravascular coagulation); TTP (thrombotic thrombocytopenic purpura) and the like.

In some embodiments, the methods and oral compositions comprising ST7S as disclosed herein can be used for the treatment of cytopenias. Significant cytopenias are associated with radiation therapies and accidental exposures, and also occur after or during chemotherapy and chemo-radiation. It has been demonstrated that the duration of neutropenia in the Acute Radiation Syndrome particularly correlates with reduced survival, with a longer duration of neutropenia correlates with decreased survival. Although G-CSF and GM-CSF can be used to reduce duration of neutropenia, they are not routinely utilized for treatment of radiation-associated neutropenias due to numerous limitations, including commercial cost, and route of administration and need for the G-CSF and GM-CSF to be refrigerated. Accordingly, one advantage of the present invention is a method and compositions of ST7S, and in particular compositions for oral administration, which can be used to enhance pan-hematologic recovery from radiation exposures, and have advantages of reduced cost, easy administration, long shelf life and no, or minimal need for refrigeration.

Other Uses.

In some embodiments, an oral composition of ST7S and/or salt thereof can be used in methods for treatment of thrombocytopenia (deficiency in platelets), or neutropenia (deficiency in neurtrophils), anemia and the like, for example, where theses disorders are a results of any, or a combination of: exposure to radiation (e.g., accidental radiation exposure), radiation therapy, chemotherapy, and radiation as a pretreatment to ablate the immune system prior to a transplantation.

In some embodiments, an oral composition of ST7S and/or salts thereof can be used a method for accelerating the recovery of, or preventing the development of a blood cell deficiency or a blood disorder in a subject, where the subject has been exposed to any one of the following: radiation (e.g., accidental radiation exposure), radiation therapy, chemotherapy, and radiation as a pretreatment to ablate the immune system prior to a transplantation. Accordingly, in some embodiments, an oral composition comprising ST7S and/or salts thereof can be used in treating "first responders" or rescue personnel to assist a disaster recovery operation at a radiation accident, e.g., military and rescue personnel who attend to a the location of radiation accident, or are likely to be exposed to radiation at a site of a radiation accident or leakage.

In some embodiments, an oral composition of ST7S and/or salts thereof can be used a method for treating a blood cell deficiency as a complication or side effect of where the subject has been exposed to any one of the following: radiation (e.g., accidental radiation exposure), radiation therapy, chemotherapy, and radiation as a pretreatment to ablate the immune system prior to a transplantation. In some embodiments, the blood cell deficiency is a complication or side effect of AIDS (acquired immunodeficiency syndrome); ITP (immune thrombocytopenic purpura); DIC (disseminated intravascular coagulation); TTP (thrombotic thrombocytopenic purpura) and the like.

Pharmaceutical Compositions, Formulations, Oral Compositions and Effective Doses.

Administration of the compositions as described herein may be by oral, parenteral, sublingual, rectal, or enteral administration, or pulmonary absorption or topical application. Compositions can be directly or indirectly administered to the patient. Indirect administration is performed, for example, by administering the composition to cells ex vivo and subsequently introducing the treated cells to the subject, e.g., human patient. Alternatively, the cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

The compositions, e.g., ST7S can be purchased commercially and prepared as a mixed composition using techniques well-known to those of ordinary skill in the art.

Direct administration of a composition to a subject can be by oral, parenteral, sublingual, rectal such as suppository or enteral administration, or by pulmonary absorption or topical application. Parenteral administration may be by intravenous (IV) injection, subcutaneous (s.c.) injection, intramuscular (i.m) injection, intra-arterial injection, intrathecal (it) injection, intra-peritoneal (i.p) injection, or direct injection or other administration to the subject.

Alternatively, pharmaceutical compositions comprising ST7S and/or salts thereof can be added to the culture medium of cells ex vivo. In addition to the active compound, such compositions comprising ST7S and/or salts thereof can contain pharmaceutically-acceptable carriers and other ingredients known to facilitate administration and/or enhance uptake (e.g., saline, dimethyl sulfoxide, lipid, polymer, affinity-based cell specific-targeting systems). In some embodiments, a composition comprising ST7S and/or salts thereof can be incorporated in a gel, sponge, or other permeable matrix (e.g., formed as pellets or a disk) and placed in proximity to the endothelium for sustained, local release. In some embodiments, a composition comprising ST7S and/or salts thereof can be administered in a single dose or in multiple doses which are administered at different times.

Pharmaceutical compositions comprising ST7S and/or salts thereof can be administered by any known route. By way of example, a composition comprising ST7S and/or salts thereof can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration of a composition comprising ST7S and/or salts thereof can be made with the goals of achieving a favorable response in the subject with a blood disorder, e.g., thalassemia, aplastic anemia and hemaglobinapathy or a risk of developing neutropenia or cytopenia, and avoiding undue toxicity or other harm thereto (i.e., safety). Therefore, "effective" refers to such choices that involve routine manipulation of conditions to achieve a desired effect.

A bolus of the formulation of a composition comprising ST7S and/or salts thereof administered to an individual over a short time once a day is a convenient dosing schedule. Alternatively, the effective daily dose can be divided into multiple doses for purposes of administration, for example, two to twelve doses per day. Dosage levels of active ingredients in a pharmaceutical composition comprising ST7S and/or salts thereof can also be varied so as to achieve a transient or sustained concentration of the compound or derivative thereof in an individual, especially in and around the blood circulation and to result in the desired therapeutic response or protection. But it is also within the skill of the art to start doses at levels lower than required to achieve the desired therapeutic effect and to gradually increase the dosage until the desired effect is achieved.

In some embodiments, the amount of a composition comprising ST7S and/or salts thereof can be administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

Production of compounds comprising ST7S and/or salts thereof according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results aimed at increasing the proliferation of blood cells, and increasing absolute neutrophil count (ANC) can vary. Thus, minimum and maximum effective dosages vary depending on the method of administration. Increase in ANC in a subject can occur within a specific dosage range, which varies depending on, for example, the race, sex, gender, age, and overall health of the subject receiving the dosage, the route of administration, whether a composition comprising ST7S and/or salts thereof is administered in conjunction with other molecules, and the specific regimen of administration of the composition comprising ST7S and/or salts thereof. For example, in general, nasal administration requires a smaller dosage than oral, enteral, rectal, or vaginal administration.

Oral Formulations

In some embodiments, administration of the compositions as disclosed herein, e.g., comprising ST7S is in an oral formulations. Example 5 provides methods for formulating ST7 and ST7S into an oral formulation.

In some embodiments, an oral formulation of ST7 comprises trappsol and/or captisol for stability, or alternatively cyclodextrin. In some embodiments, the formulation comprises the hydroxypropyl β cyclodextrin (Trappsol) at a concentration of at least 20%, or at least about 10% or between about 10% and 30% or more than about 30%. In some embodiments, the formulation comprises sulfo butyl ether β cyclodextrin (Captisol) at a concentration of at least about 20%, or at least about 10% or between about 10% and 30% or more than about 30%. In some embodiments, an oral formulation of ST7 and salts thereof comprises a preservative, for example, methylparaben, which can be used for example at a concentration of about 0.25% for the syrup formulation in the pH range of 6-7. Applicants recommend a preservative challenge test as disclosed herein in Example 5 be conducted at a later stage and a variety of different timepoints to determine the optimal concentration of methylparaben based on the results of the preservative challenge test.

In some embodiments, an oral formulation of ST7 and/or salts thereof can also comprise a sweetener, for example, an oral formulation of ST7 and salts thereof can be formulated as a syrup, for example, as disclosed in Example 5, using any sweetener commonly known to one of ordinary skill in the art, and in different combinations and percentage of the formulation. Exemplary sweeteners include, but are not limited to, Sucrose syrup, High Fructose Corn syrup, Sodium saccharin, Aspartame, Acesulfame and Sucralose. In some embodiments, an oral formulation of ST7 and/or salts thereof comprises at least one sweetener(s) or a combination of any sweeteners and a stabilizer, e.g., but not limited to Trappsol.

In some embodiments, an oral formulation of ST7 and/or salts thereof comprises at least one, or any combination of High Fructose Corn syrup, Sodium saccharin, Aspartame, Acesulfame or Sucralose. Without wishing to be bound by theory, High Fructose corn syrup was found to have a better taste-masking effect than Sucrose syrup. Sodium saccharin was found to impart greater initial sweetness than Aspartame but provided a very bitter after-taste. Acesulfame by itself provided a good initial sweetness with bitter after-taste but in combination with Sucralose provided a lingering sweet after-taste. In some embodiments, an oral formulation of ST7 and/or salts thereof comprises a combination of about 35% High Fructose Corn syrup, about 0.25% Sucralose and about 0.75% Acesulfame potassium, and about 20% Trappsol.

In some embodiments, an oral formulation of ST7 and/or salts thereof can also comprise a flavor, for example, any flavor known to persons of ordinary skill in the art, for example, but without limitation, Cherry, Grape, Lemon, Pineapple, Orange, Menthol, Chocolate, Mint, Chocolate mint. In some embodiments, an oral formulation of ST7 and/or salts thereof can also comprise an orange flavor and/or a chocolate flavor. In some embodiments, an oral formulation of ST7 and/or salts thereof comprise a flavors and an artificial sweetener i.e. Sucralose (1.25%) and Acesulfame potassium (0.75%), as well as high fructose corn syrup and Trappsol. In some embodiments, an oral formulation of ST7 and/or salts thereof can also comprise about at least 5-10% orange flavor, e.g., about at least 5%, or at least about 6%, or at least about 7%, or at least about 8%, or at least about 9%, or at least about 10 or more than about 10% Orange flavor.

In some embodiments, an oral formulation of ST7 (sodium α-Methyl Hydrocinnamate) and/or salts thereof is optimized for flavor, sweetness and bioavailability of ST7S. In some embodiments, an oral formulation of ST7 (sodium α-Methyl Hydrocinnamate) comprises the following agents in the following composition:

| | |
|---|---|
| Sodium α-Methyl Hydrocinnamate | 20% w/v (16.7% w/w) |
| Methylparaben | 0.25% w/w |
| High Fructose Corn syrup | 35% w/w |
| Trappsol (hydroxypropyl β cyclodextrin) | 20% w/w |
| Sucralose | 1.25% w/w |
| Acesulfame potassium | 0.75% w/w |
| Orange flavor | 8.0% w/w |
| Coloring agent(FD&C Yellow # 6) | 0.03% w/w |
| Deionized Water | q.s. 100 mL |

In an alternative embodiment, for oral and/or enteral formulations of a composition comprising ST7S and/or salts thereof, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982, which are all incorporated herein in their entirety by reference.

Examples of solid carriers include starch, sugar, bentonite, silica, and other commonly used carriers. Further non-limiting examples of carriers and diluents which can be used in the formulations of the present invention include saline, syrup, dextrose, and water.

Enteric Coated Formulation

In some embodiments, oral formulations of a composition comprising ST7S and/or salts thereof can be in the form of a tablet formulation, for example, comprising ST7S and/or salts thereof with an enteric polymer casing. An example of such a preparation can be found in WO2005/021002, which is incorporated herein in its entirety by reference. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropylcellulose, polyvinylpyrrolidone, pre-gelatinised starch or gum acacia or mixtures thereof; disintegrants such as microcrystalline cellulose (fulfilling both binder and disintegrant functions) crosslinked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilizers such as desiccating amorphous silica, coloring agents, flavors etc. In some embodiments, a tablet comprises lactose as diluent. When a binder is present, it is preferably hydroxypropylmethyl cellulose. In some embodiments, a tablet comprises magnesium stearate as lubricant. In some embodiments, a tablet comprises croscarmellose sodium as disintegrant, or can comprises a microcrystalline cellulose.

In some embodiments, a diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

In some embodiments, the active ingredient, e.g., ST7S and/or a salts thereof comprises between 10 and 50% of the weight of the core, more preferably between 15 and 35% of the weight of the core. (calculated as free base equivalent). The core can contain any therapeutically suitable dosage level of the active ingredient e.g., ST7S and/or a salts thereof, but preferably contains up to 150 mg as free base of the active ingredient. In some embodiments, the core contains 20, 30, 40, 50, 60, 80 or 100 mg as free base of the active ingredient. The active ingredient e.g., ST7S and/or a salts thereof can be present as the free base, or as any pharmaceutically acceptable salt. If the active ingredient e.g., ST7S is present as a salt, the weight is adjusted such that the tablet contains the desired amount of active ingredient, calculated as free base of the salt. In some embodiments, the active ingredient e.g., ST7S is present as a hydrochloride salt.

In some embodiments, the core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

In some embodiments, the core can be surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1, 2-, 3, 4-diepoxybutane. The casing can also include starch and/or dextrin.

In some embodiments, an enteric coating materials are the commercially available EUDRAGIT® enteric polymers such as EUDRAGIT® L, EUDRAGIT® S and EUDRAGIT® NE, used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX® or CITROFLEX® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

In some embodiments, a casing can also include an anti-tack agent such as talc, silica or glyceryl monostearate. In some embodiments, an anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an OPADRY coating, and particularly preferably it is Opadry White OY-S-28876.

In one embodiment, the pharmaceutically active ingredient is ST7S or a salt thereof.

In some embodiments, an example of an enteric-coated formulation as described in WO2005/021002, comprises varying amounts of ST7S. In that example, lactose monohydrate, microcrystalline cellulose, the active ingredient, the hydroxypropyl methyl cellulose and half of the croscarmellose sodium were screened into a 10 Liter Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric-coated preparations of this sort can be prepared by one skilled in the art, using these materials or their equivalents.

Other Formulations and Routes of Administration

In alternative embodiments, the compositions as disclosed herein is by an infusion pump (to infuse, for example, the compositions as disclosed herein into the subject's circulatory system) is generally used intravenously, although subcutaneous, arterial, and epidural infusions are occasionally used. Injectable forms of administration are sometimes preferred for maximal effect. When long-term administration by injection is necessary, medi-ports, in-dwelling catheters, or automatic pumping mechanisms are also preferred, wherein direct and immediate access is provided to the arteries in and around the heart and other major organs and organ systems.

In some embodiments, compositions as disclosed herein comprising ST7S and/or salts thereof can be administered to a specific site may be by transdermal transfusion, such as with a transdermal patch, by direct contact to the cells or tissue, if accessible, such as a skin tumor, or by administration to an internal site through an incision or some other artificial opening into the body.

Alternatively, in some embodiments, compositions as disclosed herein comprising ST7S and/or salts thereof can also be administered to the nasal passages as a spray. Diseases localized to the head and brain area are treatable in this fashion, as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. For example, administration of the compositions as disclosed herein comprising ST7S and/or salts thereof to a subject is preferably oral. As a result, the subject can undergo administration of a composition comprising ST7S and/or salts at home.

As indicated above, orally active compositions comprising ST7S and/or salts thereof are preferred for at least a portion of the cycle of therapy, as oral administration is usually the safest, most convenient, and economical mode of drug delivery. Consequently, compositions as disclosed herein comprising ST7S and/or salts thereof can be modified to increase their oral bioavailable by reducing or eliminating their polarity. This can often be accomplished by formulating a composition with a complimentary reagent that neutralizes its polarity, or by modifying the compound with a neutralizing chemical group. Oral bioavailability is also a problem, because drugs are exposed to the extremes of gastric pH and gastric enzymes. Accordingly, problems associated with oral bioavailability can be overcome by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

In some embodiments, the compositions as disclosed herein comprising ST7S and/or salts thereof can be used in combination with other agents to maximize the effect of the compositions administered in an additive or synergistic manner. Accordingly, compositions as disclosed herein comprising ST7S and/or salts thereof can also comprise proteinaceous agents such as growth factors and/or cytokines. Such proteinaceous agents may also be aminated, glycosylated, acylated, neutralized, phosphorylated, or otherwise derivatized to form compositions that are more suitable for the method of administration to the patient or for increased stability during shipping or storage. Cytokines that are useful to be included in the compositions comprising ST7S and/or salts thereof include, but are not limited to, growth factors such as B cell growth factor (BCGF), fibroblast-derived growth factor (FDGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). In some embodiments, other agents such as differentiating agents may be useful in combination with a composition as disclosed herein comprising ST7S and/or salts thereof to prevent or treat a neoplastic disorder. Other differentiating agents include B cell differentiating factor (BCDF), erythropoietin (EPO), steel factor, activin, inhibin, the bone morphogenic proteins (BMPs), retinoic acid or retinoic acid derivatives such as retinol, the prostaglandins, and TPA.

In some embodiments, cytokines and related antigens can be used in combination with a composition as disclosed herein comprising ST7S and/or salts thereof, for example, cytokines such as, but not limited to, tumor necrosis factor (TNF), the interleukins IL-1, IL-2, 11-3, IL-4, IL-5, IL-6, etc., recombinant IL receptors, growth factors, colony stimulating factors, erythropoietin (EPO), the interferon (IFN) proteins IFN-α, IFN-β, and IFN-γ; cyclic AMP including dibutyryl cyclic AMP, hemin, DMSO, hydroxyurea, hypoxanthine, glucocorticoid hormones, and cytosine arabinoside. Therapies using combinations of these agents would be safe and effective therapies against malignancies and other forms of cancer.

Compositions as disclosed herein comprising ST7S and/or salts thereof can be physiologically stable at therapeutically effective concentrations. Physiological stable compounds of ST7S or salts thereof not break down or otherwise become ineffective upon administration to a subject or prior to having a desired effect. Compounds of ST7S that are structurally resistant to catabolism, and, thus, physiologically stable, or coupled by electrostatic or covalent bonds to specific reagents to increase physiological stability. Such reagents include amino acids such as arginine, glycine, alanine, asparagine, glutamine, histidine, or lysine, nucleic acids including nucleosides or nucleotides, or substituents such as carbohydrates, saccharides and polysaccharides, lipids, fatty acids, proteins, or protein fragments. Useful coupling partners include, for example, glycol, such as polyethylene glycol, glucose, glycerol, glycerin, and other related substances.

In some embodiments, compositions as disclosed herein comprising ST7S and/or salts thereof are used in combination with other agents. For example, where the compositions as disclosed herein comprising ST7S and/or salts thereof are being used to increase platelets or neutrophils, or increase blood cell proliferation, after, for example, chemotherapy or radiation treatment, a combination therapy can include administering a composition comprising ST7S and/or salts thereof and an additional agent, e.g., an anti-cancer treatments. Such an agent, e.g, anti-cancer agent can be an agent that decreases growth of tumor after the anti-cancer effects of other therapies have decreased. The additional agent or therapy can also be another anti-viral or anti-cancer agent or therapy.

Physiological stability of a composition comprising ST7S and/or salts thereof can be measured from a number of parameters such as the half-life of the ST7S compound or salts thereof, or the half-life of active metabolic products derived from the ST7S compound or salts thereof. In some embodiments, compositions comprising ST7S and/or salts thereof have in vivo half-lives of greater than about fifteen minutes, greater than about one hour, greater than about two hours, and greater than about four hours, eight hours, twelve hours, or longer. A compound of ST7S or its salts is stable using this criteria, however, physiological stability can also be measured by observing the duration of biological effects on the patient. Clinical symptoms that are important from the patient's perspective include a reduced frequency or duration, or elimination of the need for transfusions or chelation therapy. Preferably, a stable composition comprising ST7S and/or salts thereof has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions as disclosed herein comprising ST7S and/or salts thereof are also not significantly biotransformed, degraded, or excreted by catabolic processes associated with metabolism. Although there may be some biotransformation, degradation, or excretion, these functions are not significant, if the composition is able to exert its desired effect.

In some embodiments, compositions as disclosed herein comprising ST7S and/or salts thereof are also safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures, and other central nervous system difficulties, fever, bleeding or hemorrhaging, serum abnormalities, and respiratory difficulties.

Compositions useful for treating blood disorders preferably do not substantially affect the viability of a blood cell such as a normal mammalian blood cell. Normal cell viability or the viability of blood cell, e.g., hematopoietic cell can be determined from analyzing the effects of the composition on one or more biological processes of the blood or hematopoietic cell.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

Administration of the composition comprising ST7S and/or salts thereof to a subject according to a method of the invention may be for prophylaxis, or alternatively, for therapeutic treatment of a subject diagnosed with a blood disorder as disclosed herein or low platelet count or neutropenia.

In some embodiments, the composition comprising ST7S and/or salts thereof can be used in prophylaxis treatment, for example, where the subject has been diagnosed with cancer and will undergo chemotherapy or radiation therapy for the treatment of cancer, the subject can be administered a composition comprising ST7S and/or salts thereof prior to, or concurrent with or subsequent to, the chemotherapy or radiation therapy, in order to prevent a low platelet counts which typically occur as a side-effect of the chemotherapy or radiation therapy cancer treatment.

In some embodiments, the composition comprising ST7S and/or salts thereof can be administered to an adult, an adolescent, a child, a neonate, an infant or in utero.

In some embodiments, the composition comprising ST7S and/or salts thereof can be administered according to a specific dosing regimen, e.g., in a single or multiple doses, or continuous or sporadic, or as deemed necessary based on an administration regime as determined by measuring absolute neutrophil counts (ANC) in the subject as disclosed herein in the Examples.

In some embodiments, a composition comprising ST7S and/or salts thereof can be administered to a subject via a continuous infusion throughout the cycle of therapy. Alternatively, a composition comprising ST7S and/or salts thereof can be administered to a the subject over a single span of a few to several hours per day every day throughout the first period of the cycle of therapy.

Alternatively, in some embodiments a composition comprising ST7S and/or salts thereof can be administered to a subject in a single parenteral bolus, or orally, daily for several days throughout the treatment regimen or cycle, or weekly.

In some embodiments, a composition comprising ST7S and/or salts thereof can be administered to a subject to augment the treatment of cancer, for example, where a subject is undergoing, or has undergone, or will undergo conventional cancer treatment, for example, chemotherapy, radiation therapy, antibody therapy, and/or other forms of cancer therapy. Some conventional chemotherapeutic agents that would be useful in combination therapy with the methods and compositions of the invention comprising ST7S and/or salts thereof can be administered to a subject include the cyclophosphamides such as alkylating agents, the purine and pyrimidine analogs such as mercaptopurine, the *vinca* and *vinca*-like alkaloids, the etoposides or etoposide-like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as anti-insulin and anti-androgen, the anti-estrogens such as tamoxifen, and other agents such as doxorubicin, L-asparaginase, DTIC, mAMSA, procarbazine, hexamethylmelamine, and mitoxantrone. These agents could be given simultaneously, or alternately as defined by a protocol in combination with composition comprising ST7S and/or salts thereof to a subject designed to maximize effectiveness, but minimize toxicity to the patient's body.

In some embodiments, a composition comprising ST7S and/or salts thereof can be prepared in solution as a dispersion, mixture, liquid, spray, capsule, or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil, or a relatively inert solid or liquid. Liquids, pills, capsules or tablets administered orally may also include flavoring agents to increase palatability. Additionally, in some embodiments, a composition comprising ST7S and/or salts thereof can further comprise agents to increase shelf-life, such as preservatives, anti-oxidants, and other components necessary and suitable for manufacture and distribution of the composition. Compositions comprising ST7S and/or salts thereof can further comprise a pharmaceutically acceptable carrier or excipient. Carriers are chemical or multi-chemical compounds that do not significantly alter or affect the active ingredients of the compositions. Examples include water, alcohols such as glycerol and polyethylene glycol, glycerin, oils, salts such as sodium, potassium, magnesium, and ammonium, fatty acids, saccharides, or polysaccharides. Carriers may be single substances or chemical or physical combinations of these substances.

Administration Therapy

In some embodiments, a composition comprising ST7S and/or salts thereof can contain chemicals that are substantially non-toxic. Substantially non-toxic means that the composition, although possibly possessing some degree of toxicity, is not harmful to the long-term health of the patient. Although the active component of the composition may not be toxic at the required levels, there may also be problems associated with administering the necessary volume or amount of the final form of the composition to the patient. For example, if composition comprising ST7S contains a salt, although the active ingredient may be at a concentration that is safe and effective, there can be a harmful build-up of sodium, potassium, or another ion. With a reduced requirement for the composition or at least the active component of that composition, the likelihood of such problems can be reduced or even eliminated. Consequently, although patients may suffer minor or short term detrimental side-effects, the advantages of taking the composition outweigh the negative consequences.

In some embodiments, treatment of a subject with a composition comprising ST7S and/or salts thereof can be according to the methods as disclosed herein can be therapeutic treatment, e.g., a method of treatment of a blood disorder in a subject, for example, a subject with neutropenia or low platelet count. In some embodiments, therapeutic treatment involves administration of a composition comprising ST7S and/or salts thereof according to the methods as disclosed herein to a patient suffering from one or more symptoms of or having been diagnosed as being afflicted with a blood disease or disorder. Relief and even partial relief from one or more of a symptom or a blood disorder may correspond to an increased life span or, simply, an increased quality of life. Further, treatments that alleviate a pathological symptom can allow for other treatments to be administered.

In alternative embodiments, the treatment of a subject with a composition comprising ST7S and/or salts thereof can be according to the methods as disclosed herein can be a prophylactic treatment, for example, to prevent low platelet count of a subject with cancer which is, or has or will undergo cancer treatment, such as for example chemotherapy, radiotherapy and the like. In some embodiments, prophylactic treatments involve administration of a composition comprising ST7S and/or salts thereof according to a method of the invention to a patient having a been recommended to have, or having undergone a cancer treatment, where it is desirable to prevent the loss or decrease of white blood cells in the subject as a side-effect of the cancer treatment. Administration of a composition comprising ST7S and/or salts thereof can begin at the beginning or after, or during (e.g., concurrent with) administration of a cancer therapy (e.g., chemotherapy, radiation therapy) etc., and can continue, if necessary, after cancer treatment, and if necessary for life. In some embodiments, prophylactic treatment is useful where a subject is likely to be exposed to radiation, for example, subjects who are in or located near an area of a radiation disaster accident, or subjects who are working in a recovery effort in an area that has had a radiation disaster or working in or near a radiation exposure. As demonstrated herein, both prophylactic and therapeutic uses are readily acceptable, because these compounds are generally safe and non-toxic.

In some embodiments, a subject can be administered a composition comprising ST7S and/or salts thereof can be according to the methods as disclosed herein to increase hematopoietic cell proliferation, for example, to increase hematopoietic stem cell production prior to bone marrow donation. For example, similar to the administration of a mobilizing agent, such as G-CSF and GM-CSF as disclosed in U.S. Pat. No. 6,261,549 and U.S. Patent Application 2009/0155225 (which are incorporated herein in their entirety by reference) to increase hematopoietic cell and hematopoietic stem cell production in subjects, herein, a composition comprising ST7S and/or salts thereof can be administered to a donor subject, for example, to increase hematopoietic cells prior to bone marrow donation, or alternatively a bone marrow stem cell donation. Accordingly, in some embodiments, administration of a composition comprising ST7S and/or salts thereof according to a methods as disclosed herein to a subject who will donate bone marrow, or bone marrow-derived stem cells, or blood, where it is desirable to increase hematopoietic cells and/or white blood cells in the donor subject prior to the donation.

Doses of Administration

The amount of α-methyl-hydrocinnamic acid that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

The data obtained from the cell culture assays and animal studies can be used in formulating a range of dosage for use in humans. The dosage of such compounds lies preferably within a range of circulating concentrations that include the ED50 (the dose therapeutically effective in 50% of the population) with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that α-methyl-hydrocinnamic acid or a prodrug thereof is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that α-methyl-hydrocinnamic acid or a metabolite thereof has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the α-methyl-hydrocinnamic acid. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The α-methyl-hydrocinnamic acid or a prodrug thereof can be administrated to a subject in combination with one or more pharmaceutically active agents. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

Administration Schedule

In some embodiments, administration of a composition comprising ST7S and/or salts can be intermittent; for example, administration can be once every two days, every three days, every five days, once a week, once or twice a month, and the like. The amount, forms, and/or amounts of the different forms of a composition comprising ST7S and/or salts can be varied at different times of administration.

Pulsed administration of one or more pharmaceutical compositions comprising ST7S and/or salts can be used for the treatment of a blood disorder in a subject, e.g., but not limited to hemaglobinapathy, thalassema and aplastic anemia. In some embodiments, pulsed administration of one or more pharmaceutical compositions comprising ST7S and/or salts can be used to stimulate myelopiesis or erythropoiesis in a subject, or to increase the proliferation of hematopoietic cells, such as hemoglobin expressing cells and red blood cells, white blood cells, neutrophils and the like. Similarly, pulsed administration of one or more pharmaceutical compositions comprising ST7S and/or salts can be used for prophylactic treatment, e.g., for example, a subject who will, or has or is currently undergoing chemotherapy and chemoradiation therapy. In some embodiments, pulsed administration can be more effective than continuous treatment as pulsed doses results in an overall lower amount of compound used than would be expected from continuous administration of the same composition. Each pulse dose can be reduced and the total amount of drug administered over the course of treatment to the patient can be minimized.

With pulse therapy, in vivo levels of ST7S and/or salts thereof can drop below the level required for effective continuous treatment. Pulsed administration can reduce the amount of a composition comprising ST7S and/or salts thereof administered to the patient per dose, and/or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

In some embodiments, individual pulses can be delivered to a subject continuously over a period of several hours, such as about 2, 4, 6, 8, 10, 12, 14 or 16 hours, or several days, such as 2, 3, 4, 5, 6, or 7 days, or from about 1 hour to about 24 hours or from about 3 hours to about 9 hours. Alternatively, periodic doses can be administered in a single bolus or a small number of injections of the composition comprising ST7S and/or salts thereof over a short period of time, for example, less than 1 or 2 hours. For example, arginine butyrate can be administered over a period of 4 days with infusions for about 8 hours per day or overnight, followed by a period of 7 days of no treatment.

The interval between pulses or the interval of no delivery can be greater than 24 hours or can be greater than 48 hours, and can be for even longer such as for 3, 4, 5, 6, 7, 8, 9 or 10 days, two, three or four weeks or even longer. The interval between pulses can be determined by one of ordinary skill in the art, for example, as demonstrated herein in the Examples, by measuring absolute neutrophil count (ANC) in the subject after administration of the pulse dose, and administering a pulse when the neutrophil count reaches a certain pre-defined low threshold limit. Such pre-defined low threshold limits can be determined by one of ordinary skill in the art, and can be, for example, about 200 cells/mm$^3$ or less than 200 cells/mm$^3$ as measured by absolute neutrophil counts (ANC) (see FIG. 9). Alternatively, in some embodiments, the interval between pulses can be calculated by administering another dose of a composition comprising ST7S and/or salts thereof, and when the active component of the composition is no longer detectable in the patient prior to delivery of the next pulse. Alternatively, intervals can also be calculated from the in vivo half-life of the composition. For example, as demonstrated in FIGS. 8A and 8B, the bioavailability of an oral formulation of ST7S and/or salts thereof is available for at least about 4 hours after administration (e.g., about 113 mg/kg administered orally), or at least about 14 hours after administration (e.g., about 1.4 g administered orally to a subject). Accordingly, intervals can be calculated as greater than the in vivo half-life, or 2, 3, 4, 5 and even 10 times greater than the functional or composition half-life. Intervals can be 25, 50, 100, 150, 200, 250 300 and even 500 times the half life of the bioavailability of the oral administration of ST7S and/or salts thereof.

In some embodiments, the number of pulses in a single therapeutic regimen can be as little as two, but can be from about 5 to 10, 10 to 20, 15 to 30 or more.

In some embodiments, a subject can receive one or more compositions comprising ST7S and/or salts thereof for life according to the methods of this invention, for example, where the subject has a permanent or incurable blood disorder, e.g., an inherited blood disorder. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590, which are incorporated herein in their entirety by reference.

In one embodiment, a composition comprising ST7S and/or salts thereof can be administered to a subject for about 2, or about 3, or about 4, or about five days, or more than five days, and then a subsequently administered after an appropriate interval for an additional period of time, for example, for about 2, or about 3, or about 4, or about five days, or more than five days. Cycles of treatment may occur in immediate succession or with an interval of no treatment between cycles.

In some embodiments, a composition comprising ST7S and/or salts thereof can be administered to a subject before a chemotherapeutic treatment, or radiation treatment is administered to the subject. In alternative embodiments, a composition comprising ST7S and/or salts thereof can be co-administered to a subject concurrently with another agent or treatment regimen, e.g., concurrently with a chemotherapeutic treatment, or radiation treatment. In some embodiments, a composition comprising ST7S and/or salts thereof can be co-administered with a pharmaceutical composition comprising an comprising one or more addition agents. The pharmaceutical compositions can be provided by pulsed administration. For example, a composition comprising ST7S and/or salts thereof can be administered to a subject, followed by a chemotherapeutic treatment, or radiation treatment after an interval of time has passed, and this order of administration the same or similar time interval can be repeated, for example, at least 1, 2, 3, 4, 5, 6, 7, 8, 9, or 10 or more times.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

In some embodiments of the present invention may be defined in any of the following numbered paragraphs:

1. An oral pharmaceutical formulation comprising: (i) a pharmaceutically effective amount of an S isomer of α-methyl-hydrocinnamic acid, or a pharmaceutically acceptable salt thereof; and (ii) a pharmaceutically acceptable carrier or diluent, wherein the oral pharmaceutical formulation is in solution or a dry solid.
2. The oral pharmaceutical formulation of paragraph 1, wherein the formulation is in solution as a dispersion, mixture, liquid, spray, or capsule.
3. The oral pharmaceutical formulation of paragraph 1, wherein the formulation is a dry solid as a powder, pill, tablet, or capsule.
4. The oral pharmaceutical formulation of any of paragraphs 1-3, which further comprises a flavoring agent.
5. A method for treating a blood disorder in a subject comprising administering to the subject an oral pharmaceutical composition comprising: (i) a pharmaceutically effective amount of an S isomer of α-methyl-hydrocinnamic acid, or a pharmaceutically acceptable salt thereof; and (ii) a pharmaceutically acceptable carrier or diluent, wherein the oral pharmaceutical composition is in solution or a dry solid, and wherein the oral pharmaceutical composition is administered to the subject by oral administration, thereby treating the blood disorder in the subject.

6. The method of paragraph 5, further comprising monitoring hemoglobin-expressing cells to ensure that cell proliferation is stimulated, and that cell viability is not significantly decreased.

7. The method of any of paragraphs 5-6, further comprising obtaining the S isomer of α-methyl-hydrocinnamic acid.

8. The method of any of paragraphs 5-7, wherein the composition is in solution as a dispersion, mixture, liquid, spray, or capsule.

9. The method of any of paragraphs 5-7, wherein the composition is a dry solid as a powder, pill, tablet, or capsule.

10. The method of any of paragraphs 5-9, wherein the composition further comprises a flavoring agent.

11. The method of any of paragraphs 5-10, wherein said the blood disorder is selected from the group consisting of: hemoglobinopathy, thalassemia, neutropenia, thrombocytopenia, anemia, white blood cell deficiencies, or aplastic anemia.

12. The method of any of paragraphs 5-11, wherein the subject has been exposed to radiation, radiation therapy, chemotherapy, transplantation.

13. A method for stimulating myelopoiesis and/or erythropoiesis in a subject, comprising administering to the subject an oral pharmaceutical composition comprising: (i) a pharmaceutically effective amount of an S isomer of α-methyl-hydrocinnamic acid, or a pharmaceutically acceptable salt thereof; and (ii) a pharmaceutically acceptable carrier or diluent, wherein the oral pharmaceutical composition is in solution or a dry solid, and wherein the oral pharmaceutical composition is administered to the subject by oral administration, thereby stimulating myelopoiesis and/or erythropoiesis in the subject.

14. The method of paragraph 13, further comprising obtaining the S isomer of α-methyl-hydrocinnamic acid.

15. The method of any of paragraphs 13-14, wherein the composition is in solution as a dispersion, mixture, liquid, spray, or capsule.

16. The method of any of paragraphs 13-14, wherein the composition is a dry solid as a powder, pill, tablet, or capsule.

17. The method of any of paragraphs 13-16, wherein the composition further comprises a flavoring agent.

18. The method of any of paragraphs 13-17, wherein the method is used to treat a blood disorder.

19. The method of paragraph 18, wherein the blood disorder is caused by radiation therapy, accidental radiation exposure, radiation exposure, transplantation therapy or chemotherapy.

20. The method of paragraph 18, wherein the blood disorder is selected from the group consisting of: hemoglobinopathy, thalassemia, neutropenia, thrombocytopenia, anemia, white blood cell deficiencies, or aplastic anemia.

21. The method of any of paragraphs 5-20, wherein the pharmaceutically effective amount is 1 μg/kg of body weight to 150 mg/kg of body weight.

22. The method of any of paragraphs 5-21, wherein said administering is everyday, every third day, every fourth day, every fifth day, every sixth day, or once a week.

23. The method of any of paragraphs 5-22, wherein administering is for a period of 1 week to 1 year.

24. Use of an oral pharmaceutical composition comprising: (i) a pharmaceutically effective amount of an S isomer of α-methyl-hydrocinnamic acid, or a pharmaceutically acceptable salt thereof; and (ii) a pharmaceutically acceptable carrier or diluent, for treating a blood disorder in a subject, wherein the oral pharmaceutical composition is in solution or a dry solid, and wherein the oral pharmaceutical composition is administered to the subject by oral administration, thereby treating the blood disorder in the subject.

25. The use of paragraph 24, further comprising monitoring hemoglobin-expressing cells to ensure that cell proliferation is stimulated, and that cell viability is not significantly decreased.

26. The use of any of paragraphs 24-25, further comprising obtaining the S isomer of α-methyl-hydrocinnamic acid.

27. The use of any of paragraphs 24-26, wherein the composition is in solution as a dispersion, mixture, liquid, spray, or capsule.

28. The use of any of paragraphs 25-27, wherein the composition is a dry solid as a powder, pill, tablet, or capsule.

29. The use of any of paragraphs 24-29, wherein the composition further comprises a flavoring agent.

30. The use of any of paragraphs 23-28, wherein said the blood disorder is selected from the group consisting of: hemoglobinopathy, thalassemia, neutropenia, thrombocytopenia, anemia, white blood cell deficiencies, or aplastic anemia.

31. The use of any of paragraphs 23-28, wherein the subject has undergone radiation therapy, accidental radiation exposure, radiation exposure, transplantation therapy or chemotherapy.

32. Use of an oral an oral pharmaceutical composition comprising: (i) a pharmaceutically effective amount of an S isomer of α-methyl-hydrocinnamic acid, or a pharmaceutically acceptable salt thereof; and (ii) a pharmaceutically acceptable carrier or diluent, for stimulating myelopoiesis and/or erythropoiesis in a subject, comprising administering to the subject, wherein the oral pharmaceutical composition is in solution or a dry solid, and wherein the oral pharmaceutical composition is administered to the subject by oral administration, thereby stimulating myelopoiesis and/or erythropoiesis in the subject.

33. The use of paragraph 32, further comprising obtaining the S isomer of α-methyl-hydrocinnamic acid.

34. The use of any of paragraphs 32-33, wherein the composition is in solution as a dispersion, mixture, liquid, spray, or capsule.

35. The use of any of paragraphs 32-33, wherein the composition is a dry solid as a powder, pill, tablet, or capsule.

36. The use of any of paragraphs 32-35, wherein the composition further comprises a flavoring agent.

37. The use of any of paragraphs 32-36, wherein the use is to treat a blood disorder.

38. The use of paragraph 37, wherein the blood disorder is caused by radiation therapy, chemotherapy, transplantation therapy or exposure of the subject to radiation.

39. The use of paragraph 36, wherein the blood disorder is selected from the group consisting of: hemoglobinopathy, thalassemia, neutropenia, thrombocytopenia, anemia, white blood cell deficiencies, or aplastic anemia.

40. The use of paragraph 37, wherein the blood disorder is a deficiency in blood cells.
41. The use of paragraph 37, wherein the blood disorder is an acquired or genetic blood disorder.
42. The use of any of paragraphs 30-41, wherein the use is to prevent an acquired blood disorder or blood cell deficiency in a subject, wherein the subject will be, or has been exposed to radiation.
43. The use of paragraph 42, wherein the subject will or has undergone radiation therapy.
44. The use of paragraph 42, wherein the subject will or has been exposed to a radiation accident, chemotherapy, transplantation.
45. The use of paragraph 42, wherein the blood cell deficiency is a decrease at least one of white blood cells, platelets or red blood cells.
46. The method of any of paragraphs 24-31, wherein the pharmaceutically effective amount is 1 µg/kg of body weight to 150 mg/kg of body weight.
47. The method of any of paragraphs 24-31, wherein said administering is everyday, every third day, every fourth day, every fifth day, every sixth day, or once a week.
48. The method of any of paragraphs 24-31, wherein administering is for a period of 1 week to 1 year.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The invention can be understood more fully by reference to the following detailed description and illustrative examples, which are intended to exemplify non-limiting embodiments of the invention.

EXAMPLES

The following examples are provided for illustrative purposes only and are not intended to limit the scope of the invention.

Example 1

ST7S is shown to stimulate myelopoiesis and erythropoiesis in animal subjects. In vitro testing performed in cell culture (data not shown) revealed stimulation of erythropoiesis and myelopoiesis for about 50 µM S isomer vs. about 200 µM racemate. Thus, the employed concentration of S isomer is about 4-fold lower than that of racemate to achieve similar degrees of erythropoiesis and myelopoiesis. Similar in vitro results were found for the R isomer of alpha-methyl-hydrocinnamic acid in comparison with the racemate.

Example 2

ST7 is a Multi-lineage Hematopoietic Stimulant.

The inventors surprisingly discovered that during evaluation of small molecules to induce fetal globin expression, a few compounds were incidentally discovered to stimulate production of multi-lineage progenitors both in vitro & increase multi-lineage cell counts in vivo in at least 2 species, non-human primates, humans and rodent animal models.

Administration of ST7 to mice resulted in a significant increase in total hemoglobin level (2.5 g/dL), and an absolute increase in hematocrit level of 7 percentage points (28% of baseline) (see FIGS. 1A-1C). In particular, ST7 was administered once daily to mice for 5 days, and results in a significant increase in hematocrit by day 14. Similarly FIG. 1D, oral administration of ST7 (50 mg/kg per day for 5 days a week over 3 weeks) by daily phlebotomy to baboons that had chronic anemia demonstrated an increase in total hemoglobin level (2.5 g/dL), and absolute increase in hematocrit level of 7 percentage points (28% of baseline).

Figure 2A:
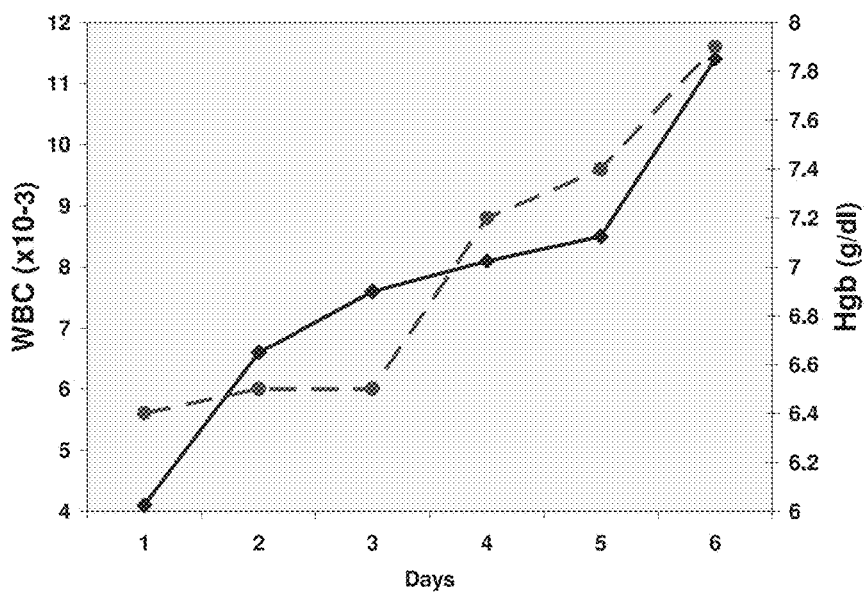
FIG. 2A-2B show that ST7 Stimulates myeloiesis.
Figure 2B:
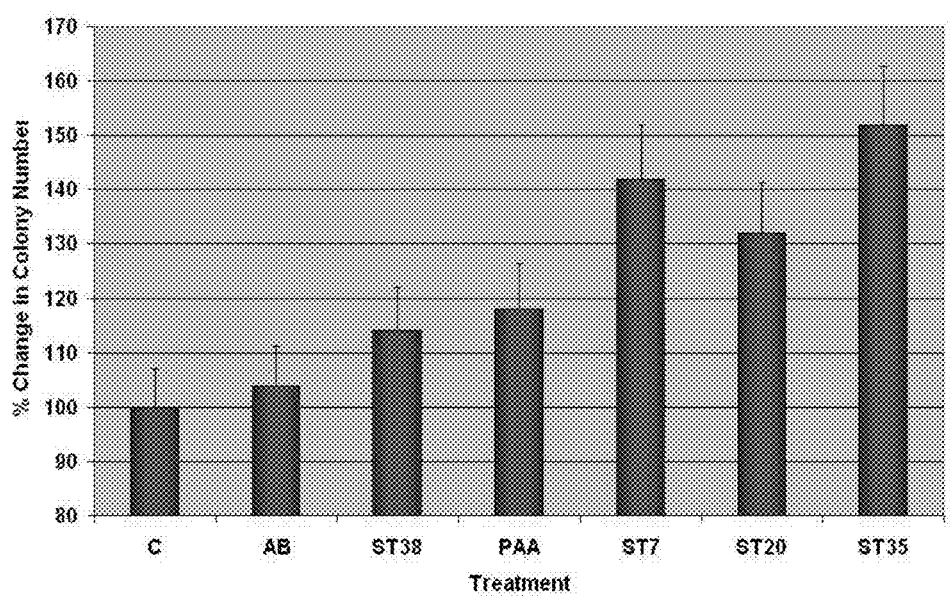

Herein, ST7 was also demonstrated to stimulate myeloiesis. In particular, oral administration of ST7 to a baboon results in a 3-fold stimulation of WBC count over 6 days (FIG. 2A). In a CFU-GEM cononly forming unit assay, the growth of human hematopoietic cultures treated with ST7 and other SCFD derivatives demonstrates that ST7 increases CFU-GM colony formation (FIG. 2B).

Figure 3A:
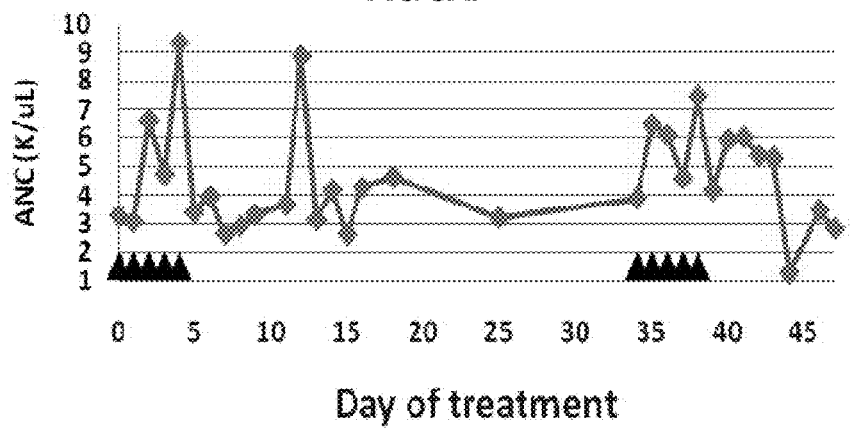
FIGS. 3A-3C show Neutrophil counts increase with ST7S in baboons.
Figure 3B:
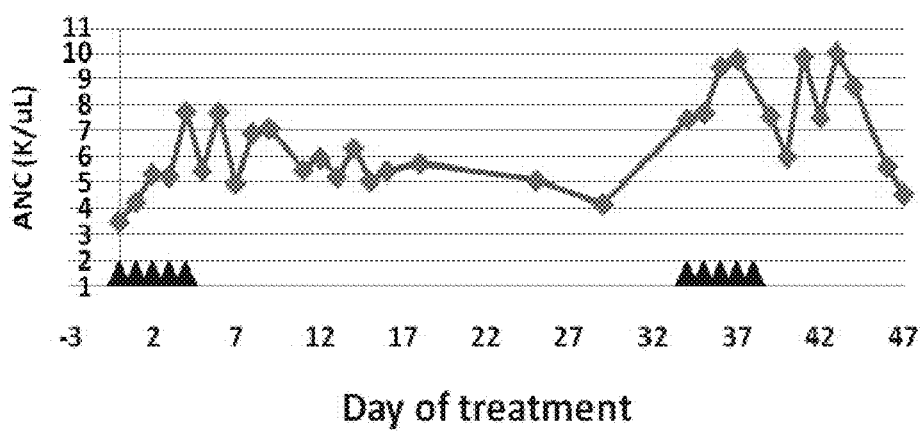
Figure 3C:
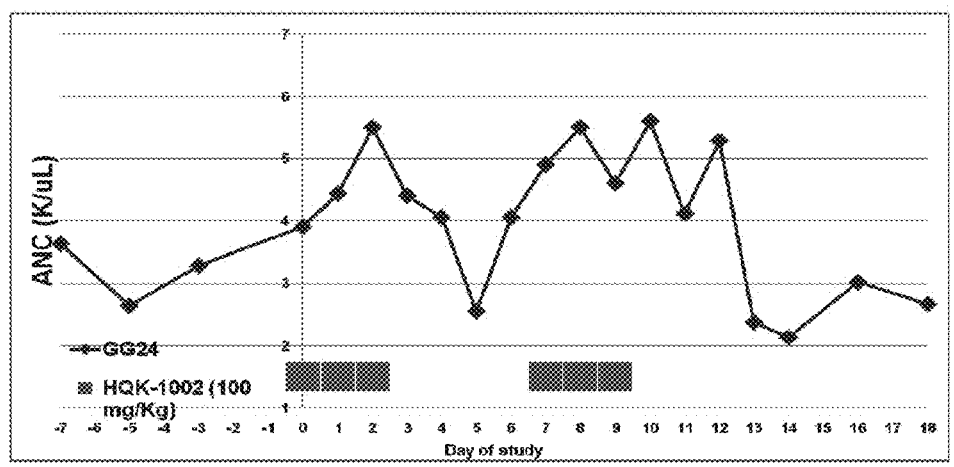

Administration of ST7S increases neutrophil counts in baboons in vivo, as demonstrated over a long-term time period (47 days, FIGS. 3A-3B), when ST7S was administered in pulse of 4 days at 1-5 days and 34-38 days. Similarly, short-term administration (e.g., 2 day administration) of ST7S for 4-5 days increases neutrophil counts in baboons in vivo when ST7S is administered at 100 mg/kg at day 0-2 and day 7-9.

Figure 4A:
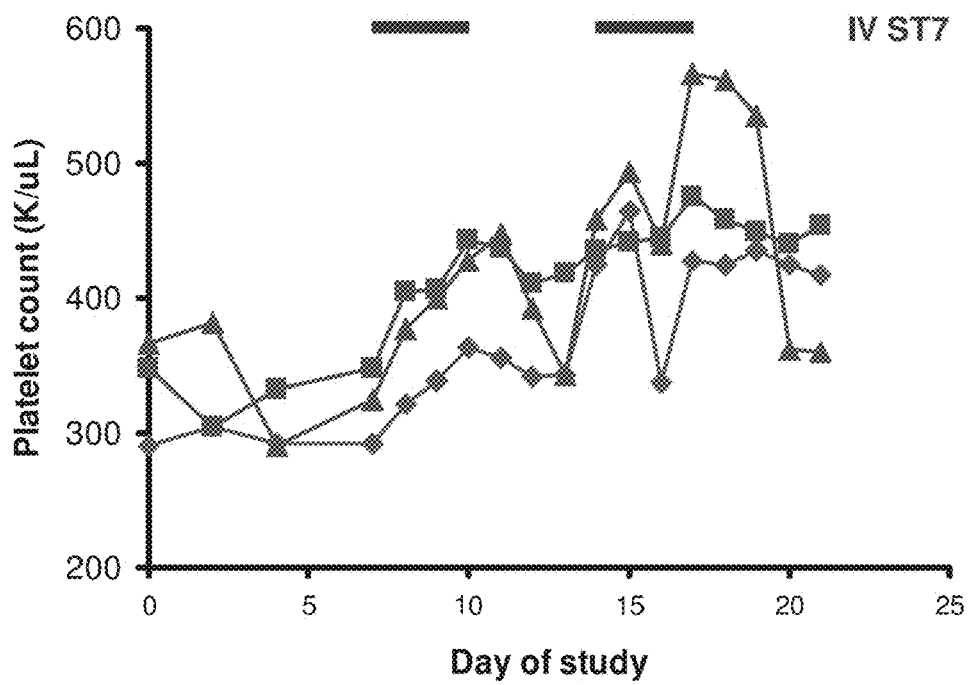
FIG. 4A-4B shows ST7 enhances platelet counts in non-human primates.
Figure 4B:
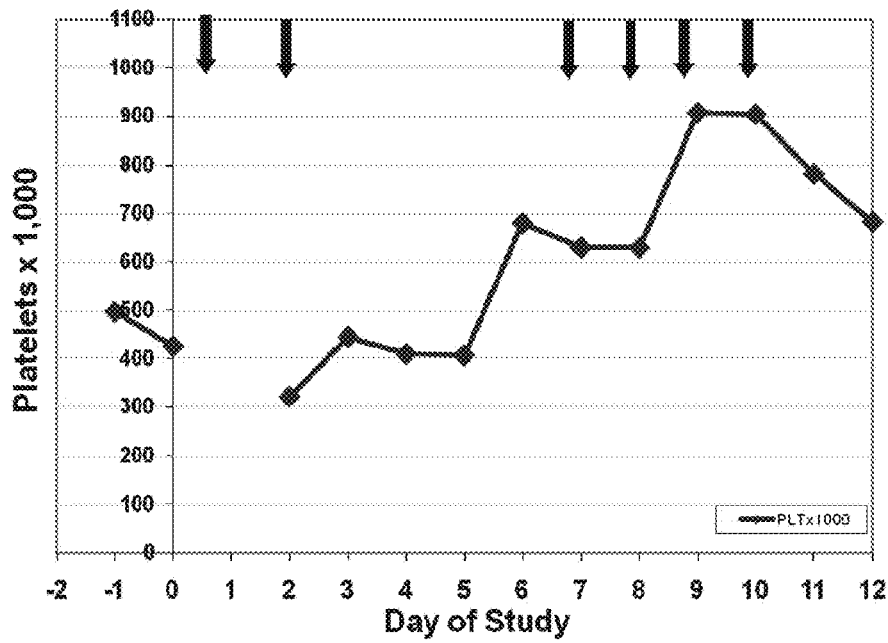

Administration of ST7 also increases platelet levels after administration to non-human primates. For example, IV administration of ST7 to 3 baboons at two time-points, on days 1-3 and 7-9 results in a stimulation of platelet count in all animals (FIG. 4A). In particular, administration of ST7S to one baboon (Baboon No. 08505) demonstrated at least a 3-fold increase in platelet counts (FIG. 4B).

Figure 5A:
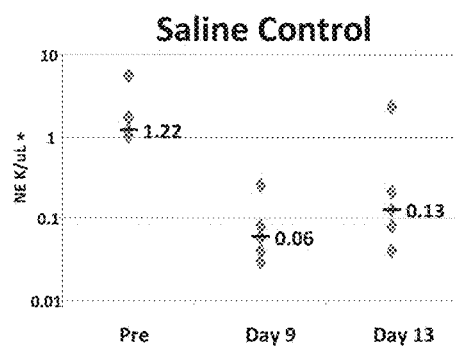
FIG. 5A-5C shows ST7 also Enhances Myeloid Recovery in a Chemotherapy-Induced Neutropenia Murine Model. Mice were treated with 5-FU on day 0, then received daily SC injection of saline or ST7 or G-CSF beginning on Day 1 and absolute neutrophil counts (ANC) were assessed on days 0, 9 and 13.
Figure 5B:
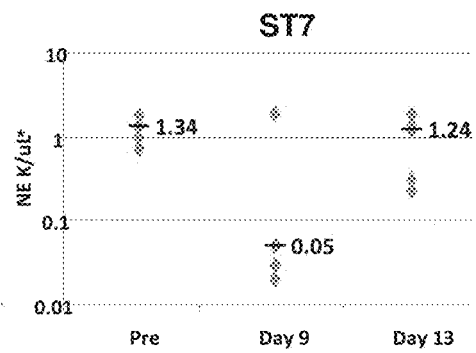
Figure 5C:
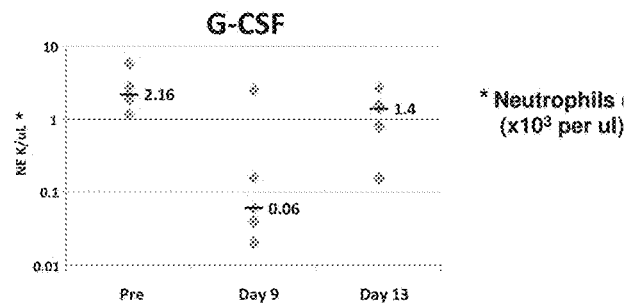
Figure 6:
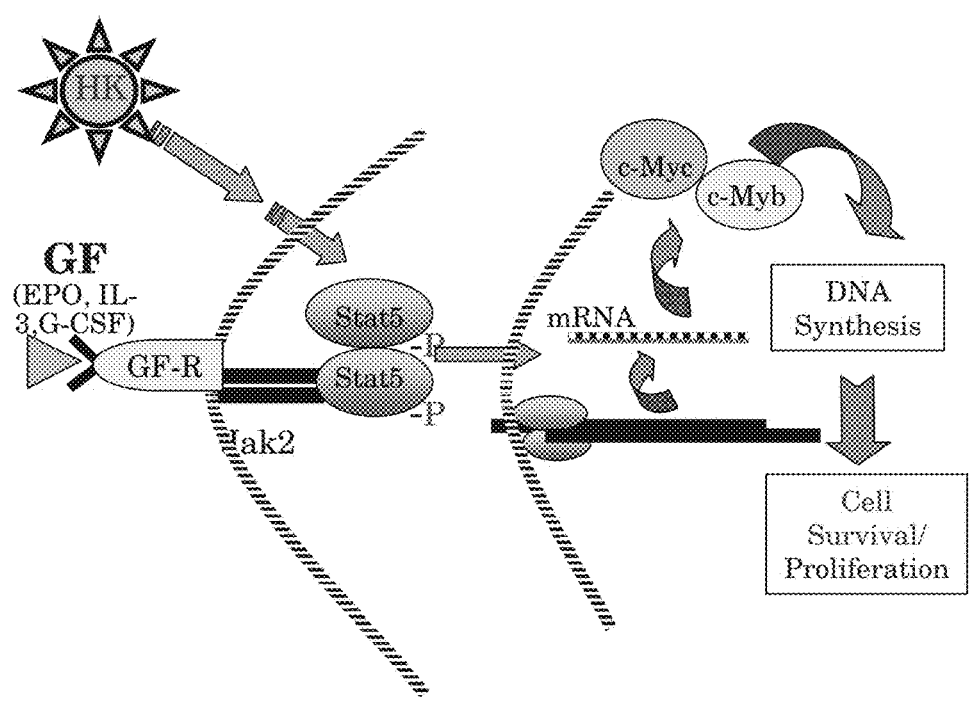
FIG. 6 is a schematic showing the mechanism of action of ST7 prolonging action of STAT-5 phosphorylation. HKs act through growth factor (GF) signaling pathway to prolong Stat-5 activation, but does not affect ras signaling or receptors.

Additionally, administration of ST7 also enhances Myeloid Recovery in a Chemotherapy-Induced Neutropenia Murine Model. Mice were treated with 5-FU on day 0, then received daily SC injection of saline (control) or ST7 or G-CSF beginning on Day 1 and the absolute neutrophil counts (ANC) were assessed on days 0, 9 and 13. As shown in FIG. 5B, ST7 treatment accelerated recovery of ANC by day 13 as efficiently as G-CSF (see FIG. 5B), and about 7-10-fold increase in NE (K/µL) at day 13 as compared to saline control treated mice (FIG. 5A).

Figure 7A:
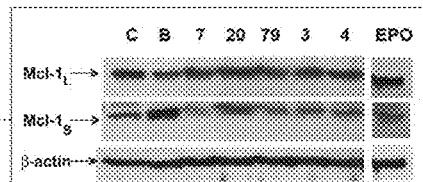
FIG. 7A-7C shows ST7 suppresses apoptosis.
Figure 7B:
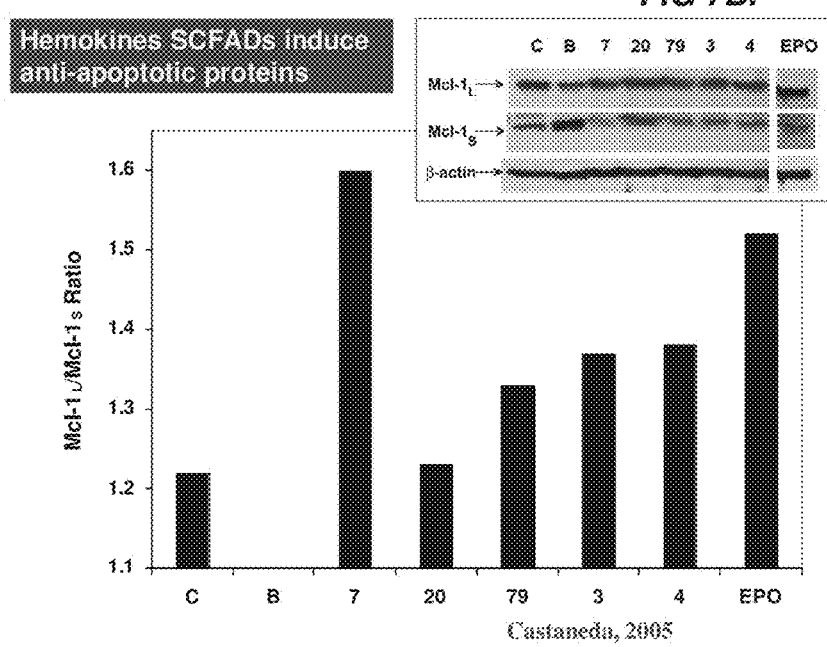
Figure 7C:
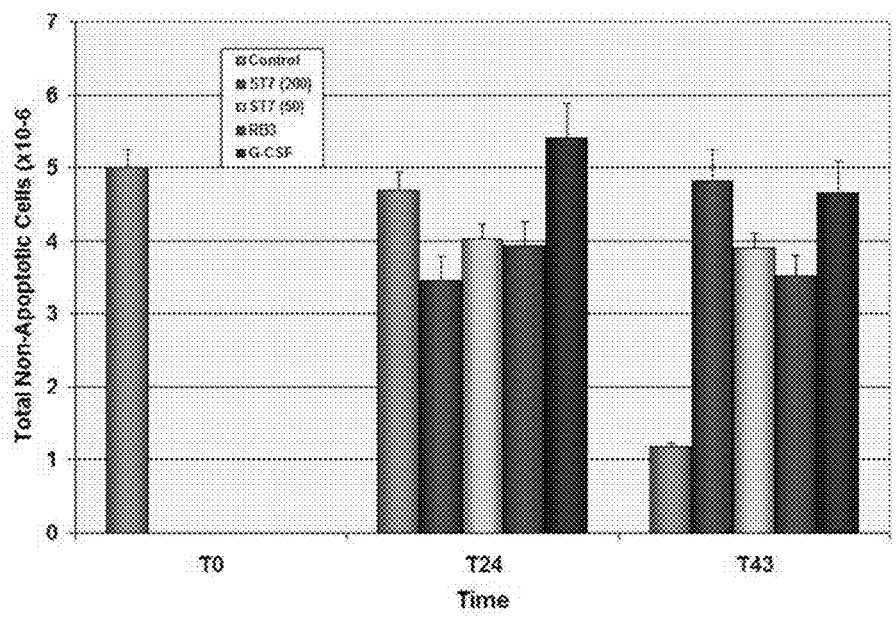

Administration of ST7 was also demonstrated to suppress apoptosis (see FIG. 7A-7B), demonstrating that the ratios of Mcl-1L to Mcl-1S are shifted towards anti-apoptotic actions after exposure to ST7. Human neutrophil survival in vitro with, or without, hemokines ST7 (200 µM), ST7 (50 µM), RB3 and G-CSF demonstrate that ST7 suppresses apoptosis in cultured normal human neutophils.

Example 3

Figure 8A:
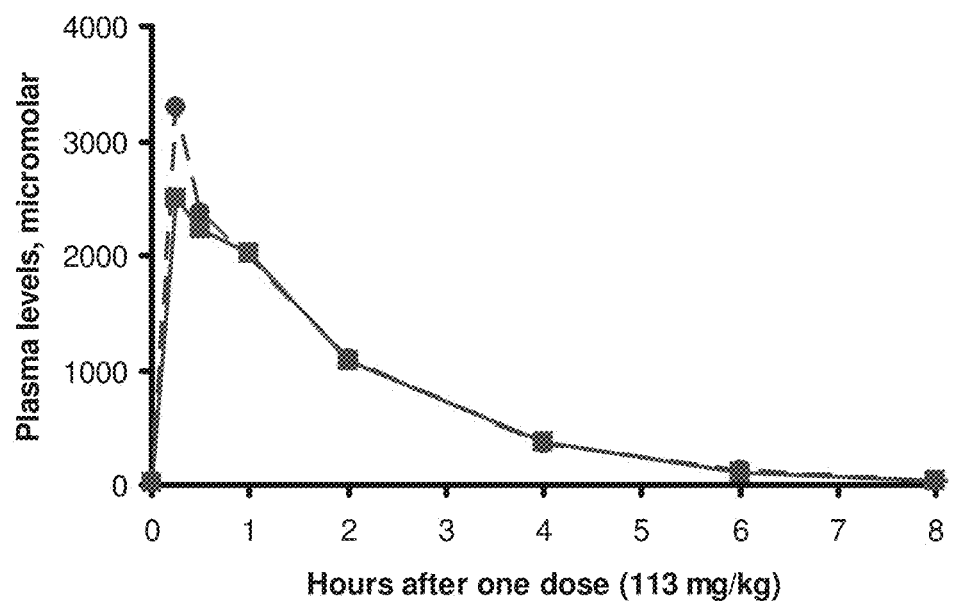
FIGS. 8A-8B show pharmaceutical and oral bioavailability of ST7.
Figure 8B:
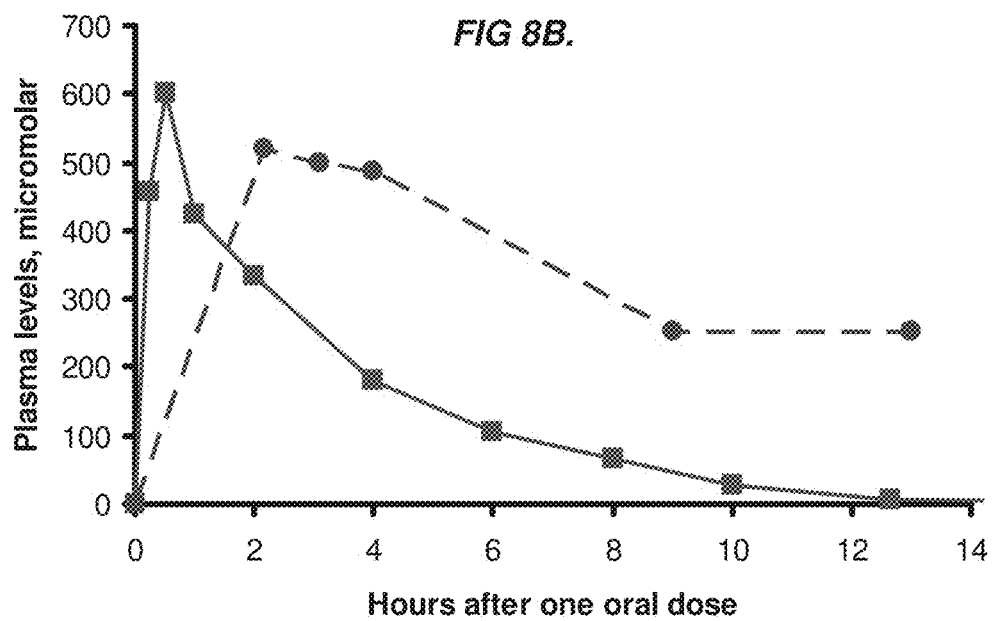

To determine if ST7 administered orally resulted in similar pharmacokinetic features as IV administration, PK profiles were evaluated in baboons. As shown in FIGS. 8A and 8B, the pharmaceutical and oral bioavailability of ST7 after oral and IV administration results in nearly identical PK profiles in non-human primates, demonstrating that >90% oral bioavailability of ST7 at a dose of 113 mg/kg (FIG. 8A). Oral administration of ST7 to a normal human subject at 1 or 1.4 grams (which is equivalent to about 20 mg/kg of an adult human dose) results in an increase in plasma levels (μM), and demonstrates that ST7 persists above the target dose for several hours after administration (FIG. 8B). Accordingly, ST7 is suitable for once/day dosing.

Example 4

Figure 9:
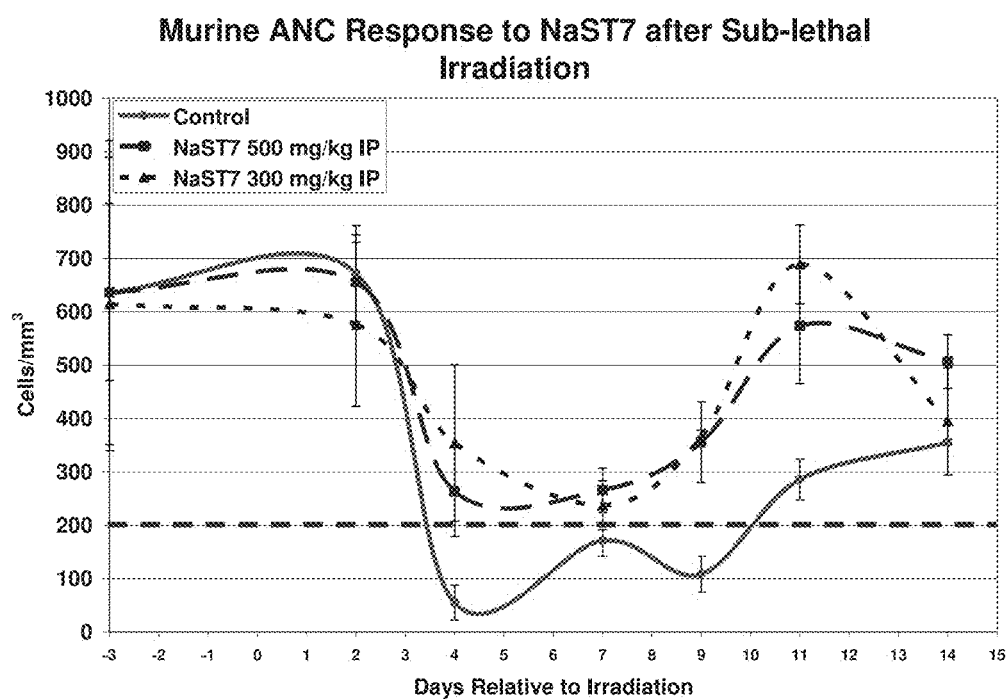
FIG. 9 shows ST7 stimulates myeloposis in a sub-lethally irradiated mouse model.
Figure 10A:
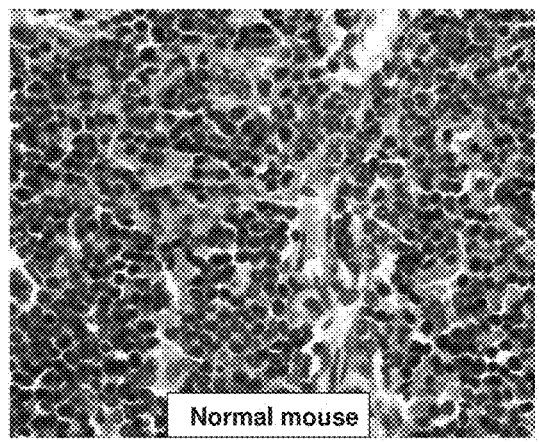
FIG. 10A-10C shows ST7S stimulates bone marrow recovery in a lethally-irradiated murine model.
Figure 10B:
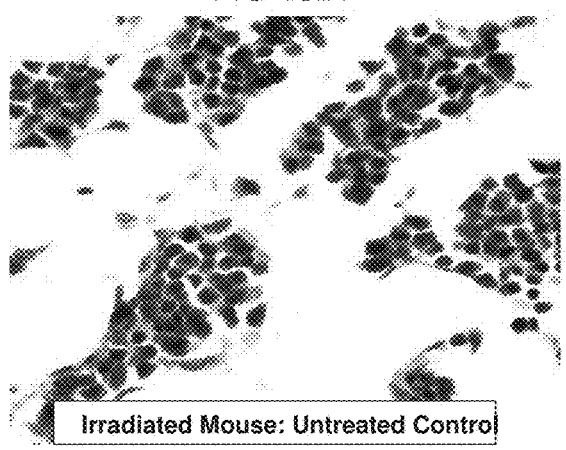
Figure 10C:
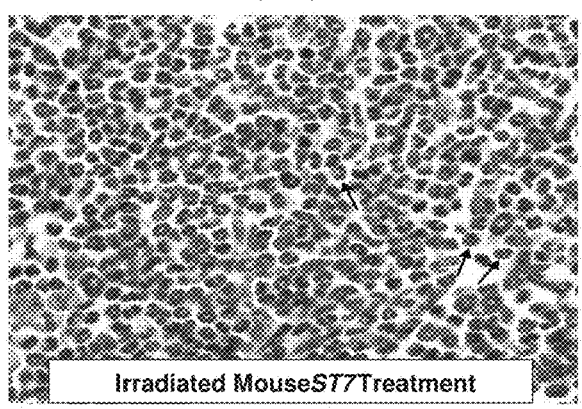

ST-7 was evaluated in a sub-lethal radiation murine model for potential effects on neutrophil recovery and was demonstrated to stimulate myeloposis in a sub-lethally irradiated mouse model. In particular, absolute neutrophil count (ANC) increased after administration of NaST7 (500 mg/kg IP and 300 mg/kg IP) after sub-lethal does of irradiation (e.g., exposure to 6 Gy irradiation on day 0). As shown in FIG. 9, daily administration of ST7 (enantiomer) was administered at two doses (500 mg/kg IP and 300 mg/kg IP), beginning day 1 and prevented the platelet level from decreasing below 200 cells/mm$^2$ at any timepoint following the sub-lethal irradiation, whereas control (saline) treated animals had an ANC of less than 200 for at least 7 days (e.g., between days 3-10). Histopathology studies of the bone marrow at day 15 following irradiation of ST7S treated animals as compared to the control (saline) treated animals demonstrates that ST7S stimulates bone marrow recovery in a lethally-irradiated murine model (FIG. 10A-10C). In particular, the bone marrow of saline treated, lethally-irradiated mice is hypocellular (FIG. 10B), whereas the bone marrow in a lethal-irradiated mouse treated with ST7S (FIG. 10C) is similar to normal non-irradiated mice (FIG. 10A), and demonstrated neutrophil differentiation (arrows, FIG. 10C).

Figure 11:
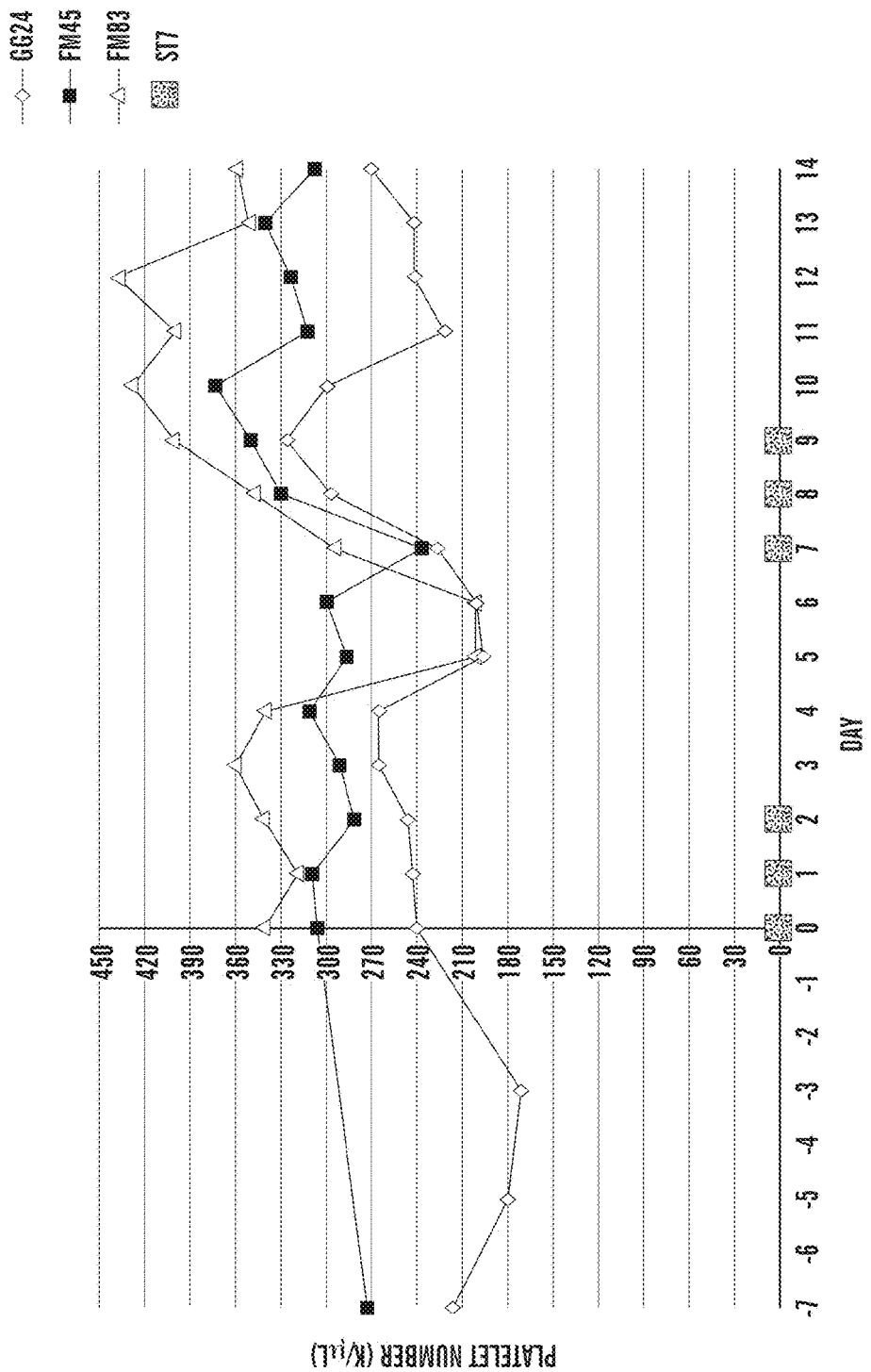
FIG. 11 shows that ST7 treatment increased platelet counts (K/µL) in nonphlebotomized nonhuman primates. ST7 was administered via IV to baboons on days 1-3 and 7-9. ST7 works as similarly in all three baboons (Baboon numbers: GG24, FM45, FM83).
Figure 12:
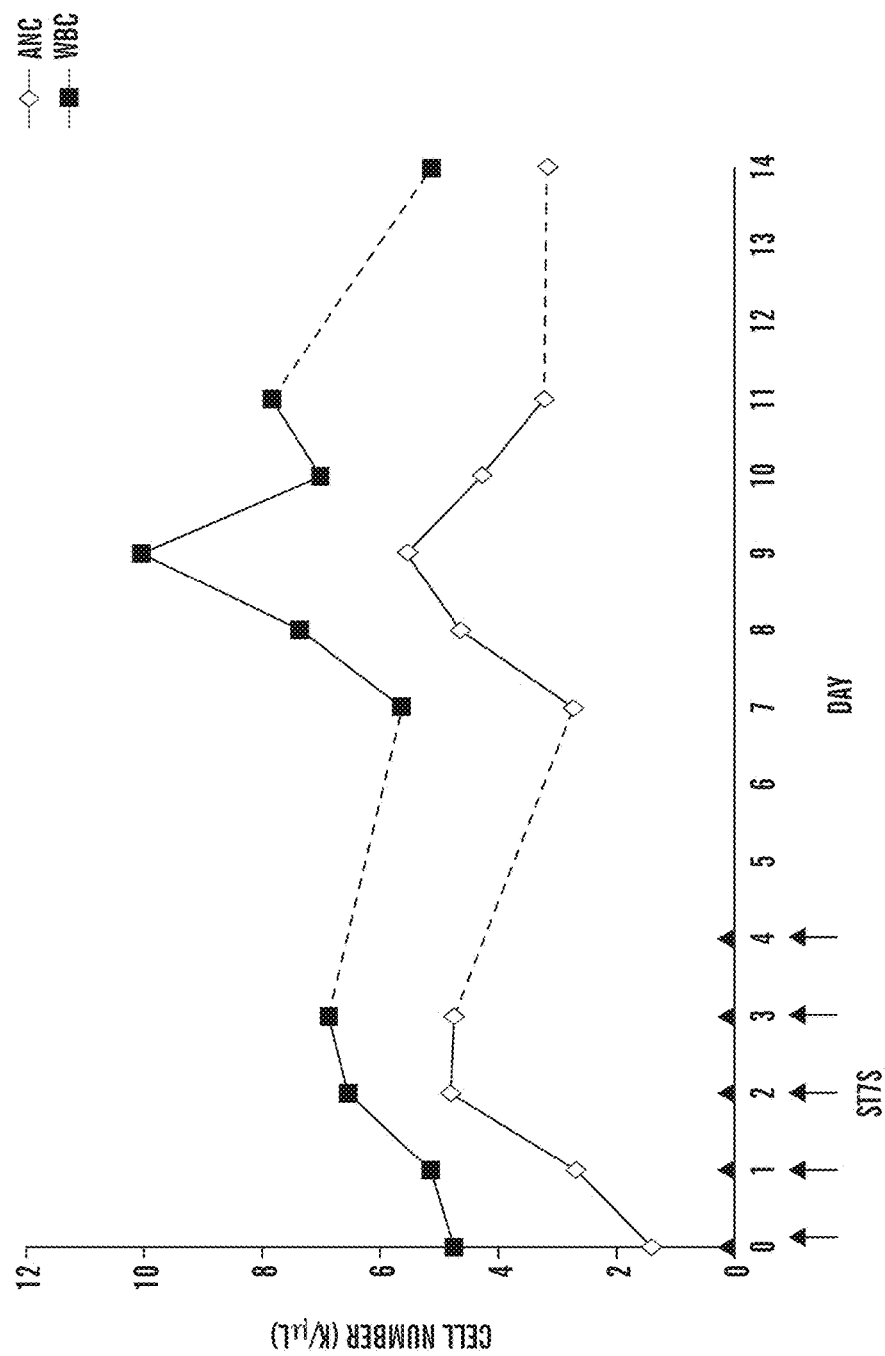
FIG. 12 shows both White blood cells (WBC) and Absolute neutrophil counts (ANC) after administration of ST7 in non-human primates.

Additionally, the platelet count of non-human primates treated with NaST7-S increased as compared to ST7 (FIG. 11).

Accordingly, it is demonstrated herein that ST7 stimulates multi-lineage hematopoietic cell production, including neutrophils, erythrocytes and platelets. ST7 stimulates multi-lineage hematopoietic cells in multiple species in vivo, including but not limited to, human, mice and non-human primates. Additionally, the inventors demonstrated herein that ST7 is bioavailable on oral administration, demonstrating PK profiles similar to IV administrating, demonstrating that administration of ST7 would be suitable with an administration regimen of at least once a daily dosing, or less than once a day dosing.

Example 5

Oral Formulation of ST7

The formulation development of an oral formulation for sodium α-methyl hydrocinnamate was produced and analyzed for solubility and stability. Additionally, the following analysis was performed:
1. Determination of pH solubility profile
2. Determination of pH stability profile
3. Selection of buffer and buffer strength
4. Selection of formulation type
5. Selection of co-solvents and complexing agents
6. Selection of preservatives
7. Selection of sweeteners
8. Selection of flavors
9. Composition of Final Formulation
10. Analytical Method development
11. Accelerated Stability study Determination of pH Solubility Profile.

Sodium a-methyl hydrocinnamate was added to DI water in excess to determine the saturation solubility in water. The samples (n=3) were shaken and vortexed for about two hours to dissolve sodium a-methyl hydrocinnamate. The clear solution was diluted and analyzed by UV at a wavelength of 258 nm to determine the amount dissolved. The saturation solubility of sodium a-methyl hydrocinnamate in water was determined to be 655 mg/mL. The pH of the saturated solution was determined to be about 10.4.

The pH of the saturated aqueous solution was successively adjusted to pH values of 8, 7, 6, and 5 using 50% v/v phosphoric acid to determine the saturation solubility of each pH. To determine the saturation solubility at each pH, the aqueous layer obtained at each pH was diluted further in water and analyzed by UV. The pH solubility data and plot are presented in Table 1 and FIG. 13A, respectively.

TABLE 1 pH Solubility data for sodium α-methyl hydrocinnamate.

| pH (average) | Appearance | Solubility, mg/mL | | | | Standard Deviation |
|---|---|---|---|---|---|---|
| | | 1 | 2 | 3 | Average | |
| 10 | Clear solution | 631.7 | 700.4 | 633.3 | 655.1 | 39.2 |
| 8 | Clear solution | 660.8 | 663.6 | 635.7 | 653.3 | 15.4 |
| 7 | Turbid solution | 653.5 | 579.7 | 443.8 | 559.0 | 106.3 |
| 6 | Separation of two phases | 2.7 | 3.6 | 2.2 | 2.8 | 0.7 |
| 5 | Separation of two phases | 1.9 | 3.8 | 1.0 | 2.2 | 1.5 |

Figure 13A:
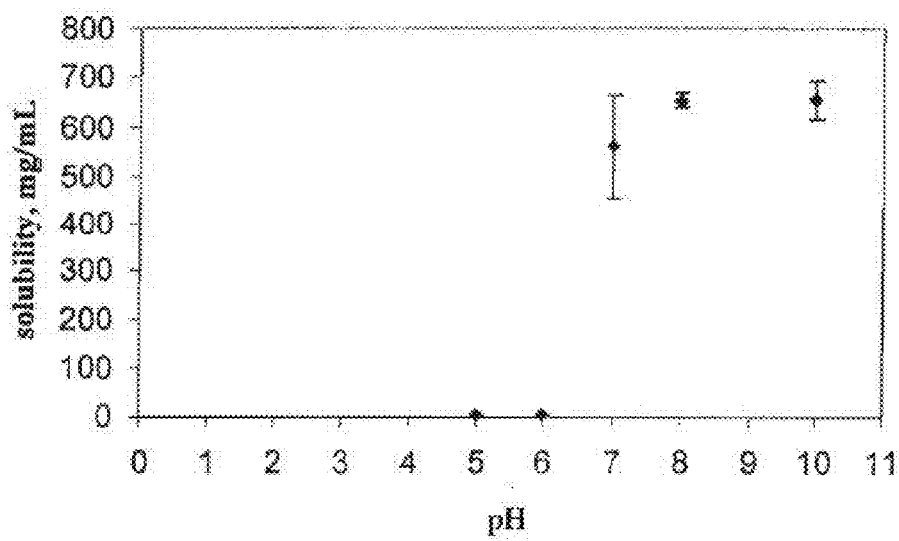
FIGS. 13A-13B shows sodium α-methyl hydrocinnamate solubility and pH stability profile.

The solubility data presented in Table 1 and FIG. 13A indicate that in order to prepare an oral formulation in the pH range of 5-7, it will be necessary to evaluate the use of co-solvents or complexing agents to achieve a target formulation concentration of 200 mg/mL of sodium α-methyl hydrocinnamate.

Determination of pH Stability

The pH stability profile was determined at pH values of 2, 5, 6, 7, 8, 9, and 13 respectively. A pH 7 phosphate buffer at a buffer concentration of 100 mM was initially prepared. Six different aliquots of this buffer were successively adjusted to pH values of 2, 4, 6, 8, 9, and 13 using either 50% v/v phosphoric acid or 1N sodium hydroxide solution. Transferred 0.2 mL of sodium α-methyl hydrocinnamate stock solution and 1 mL of alcohol into a 10.0 mL volumetric flask was made up the volume with each of the seven buffer solutions to yield a final concentration of ~4 mg/ml of sodium α-methyl hydrocinnamate.

Figure 13B:
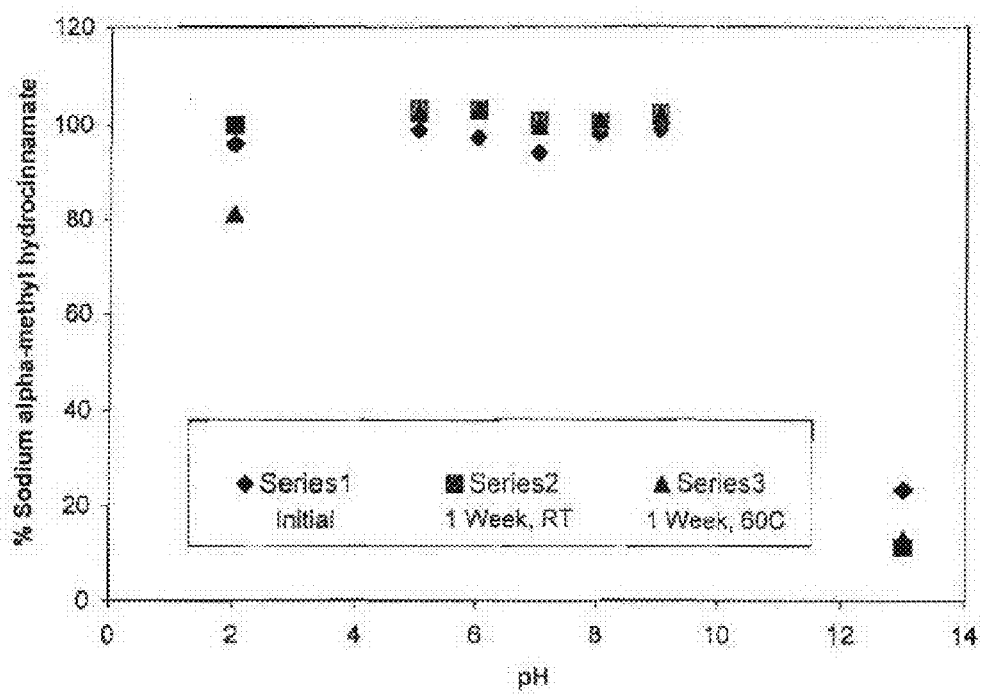

Diluted 0.5 ml of each solution to 5 mL with diluent and analysed by HLPC per AM-013-RO to determine the initial concentration of sodium α-methyl hydrocinnamate. The solution was divided into two parts, one part was kept at room temperature (RT) and the other part was kept at 60° C. to evaluate the stability of sodium α-methyl hydrocinnamate. The pH stability date is presented in Table 2. The pH stability plot is shown in FIG. 13B.

TABLE 2 pH stability Data for sodium α-methyl hydrocinnamate.

| Buffer PH | Initial pH on addition of drug | Assay, initial | Assay, 1 Week RT | Assay, 1 Week 60° C. | pH, 1 Week RT | pH, 1 Week 60° C. |
|---|---|---|---|---|---|---|
| 2 | 2 | 95.8 | 99.8 | 81.2 | 2.2 | 1.9 |
| 4* | 5* | 98.8 | 102.9 | 102.3 | 5.3 | 5.1 |
| 6 | 6 | 97.2 | 102.9 | 102.9 | 6.3 | 6.0 |
| 7 | 7 | 94.0 | 100.7 | 99.6 | 7.2 | 6.9 |
| 8 | 8 | 97.9 | 100.4 | 100.8 | 8.3 | 8.1 |
| 9 | 9 | 98.8 | 102.2 | 101.6 | 9.2 | 9.0 |
| 13 | 13 | 23.2 | 11.2 | 12.9 | 12.8 | 12.7 |

*The solution of pH on addition of the sodium salt was observed to be 5 as the pH 4 phosphate buffer did not have enough buffer capacity. All stability date therefore was reported as pH 5 instead of pH 4. Accordingly, the inventors recommend that a buffer other than phosphate buffer should be employed to evaluate the pH stability at pH values 4-5.

The pH stability data indicate that sodium a-methyl hydrocinnamate is stable over the pH range of 2-9 at room temperature for at least 1 week. About 80% degradation is observed at pH 13 initially, which reached 90% upon storage for 1 week at both room temperature and 60° C. About 20% degradation is observed in pH 2 solution stored for 1 week at 60° C. The data also indicate that sodium a-methyl hydrocinnamate is stable for at least one week over the pH range of 5 to 9 when stored at 60° C. Data also show that solution pH probably affects the extent of degradation to a greater extent than temperature.

The pH stability data obtained over the pH range employed in this study indicate that the target drug product pH for the sodium a-methyl hydrocinnamate should be in the range of 5 to 9.

Selection of Buffer and Buffer Strength

Based on the pH stability data it is recommended to formulate the oral product in the pH range of 5 to 9. Hence, three buffers were evaluated for possible use in the preparation of oral dosage form of sodium α-methyl hydrocinnamate. The pH of aqueous solution of sodium a-methyl hydrocinnamate at a target drug product concentration of 200 mg/mL is about 10. In order to prepare a palatable oral solution of sodium α-methyl hydrocinnamate, it is desired to prepare the oral solution at a pH close to that of the physiological pH in the oral cavity pH (~6).

Studies were conducted to evaluate the use of buffers and buffer strengths as it is necessary to control the pH of an oral formulation close to the initial formulation pH value if shift in pH values are observed under accelerated stability or stress conditions. The following studies were therefore conducted to evaluate buffer solutions that could possibly be used over a pH range of 5-7. Three buffers namely, acetate, citrate, and phosphate were evaluated for buffer capacity and to check their effect on the solubility of sodium a-methyl hydrocinnamate.

The sodium α-methyl hydrocinnamate was added to pH 4.7 acetate buffer (per USP) at a concentration of about 100 mg/mL. The α-methyl hydrocinnamic acid was observed to separate from the aqueous layer.

The addition of complexing agents, hydroxypropyl beta cyclodextrin (Trappsol) and sulfobutylether beta cyclodextrin (Captisol) at concentrations of about 25-30% to the acetate buffer did not result in complete miscibility of the free acid with aqueous solution. The acetate buffer was thus not used in further studies.

Solubility of sodium a-methyl hydrocinnamate and buffer capacity of pH 5 citrate buffers prepared at four different buffer concentrations were evaluated as presented in Table 3.

TABLE 3

Solubility of Sodium α-methyl Hydrocinnamate in Citrate Buffer Containing 30% cyclodextrin.

| Conc. Of sodium α-Methyl Hydrocinnamate | Citrate Buffer Concentration, M | | | |
|---|---|---|---|---|
| | 1.0 | 0.5 | 0.25 | 0.1 |
| Citrate buffer containing 30% Captisol. Initial pH: 4.9 | | | | |
| 100 mg/ml | Insoluble Turbidity: 1M > 0.5M > 0.25M | | | Clear colorless solution |
| 250 mg/ml | N/A | N/A | N/A | Clear colorless solution |
| pH | N/A | N/A | N/A | 7.3 |
| Citrate buffer containing 30% Trappsol. Initial pH: 5.1 | | | | |
| 100 mg/ml | Insoluble Turbidity: 1M > 0.5M | | Clear colorless solution | Clear colorless solution |
| 250 mg/ml | N/A | N/A | Clear colorless solution | Clear colorless solution |
| pH | N/A | N/A | 6.5 | 7.0 |

The data presented above indicate that citrate buffer containing 30% Trappsol can better dissolve sodium a-methyl hydrocinnamate at the target formulation concentration than the citrate buffer containing 30% Captisol.

Also, sodium a-methyl hydrocinnamate is observed to be not soluble in citrate buffers of high concentrations such as 0.5M and 1 M, respectively. These buffers were primarily evaluated to assess the effect on buffer capacity. The 0.25M and 0.1M buffer solutions containing 30% Trappsol can dissolve sodium a-methyl hydrocinnamate at the target formulation concentration, however, the buffer capacity is observed to be insufficient. The pH of buffer solution was observed to change by 1.5-2 units upon the addition of target concentration of sodium α-methyl hydrocinnamate. The citrate buffer was thus not used for further studies.

Phosphate buffer solutions at a target pH of 7 were prepared at buffer concentrations of 0.5M, 0.25M, and ~0.1M, respectively. The buffer solutions contained 20% cyclodextrin. The sodium α-methyl hydrocinnamate was observed to dissolve at the target formulation concentration in all of the three phosphate buffer solutions. The solubility data in phosphate buffer are presented in Table 4.

TABLE 4

Solubility of Sodium α-Methyl hydrocinnamate in Phosphate Buffer Containing 20% Cyclodextrin

| Buffer Conc. (M) | Concentration of Sodium α-Methyl hydrocinnamate | 20% Captisol | | 20% Trappsol | |
|---|---|---|---|---|---|
| | | Initial pH | Final pH * | Initial pH | Final pH * |
| ~0.1 | 250 mg/mL | 6.8 | 7.9 | 6.8 | 7.6 |
| 0.25 | 250 mg/mL | 6.3 | 7.0 | 6.3 | 6.8 |
| 0.5 | 250 mg/mL | 6.2 | 6.8 | 6.3 | 6.7 |

* Final pH = pH upon addition of Sodium α-Methyl hydrocinnamate

The data indicate that phosphate buffer concentrations of 0.25M and 0.5M show acceptable buffer capacity. In order to minimize the effect of buffer concentration on solubility of sodium α-methyl hydrocinnamate, a phosphate buffer concentration of 0.25M was chosen for further formulation development studies; to be if pH of the formulation is observed to change significantly on stability.

Selection of Formulation Type

Two types of oral formulations were considered to start with viz. oral syrup and elixir (hydro-alcoholic preparation). The formulations were prepared at the target strength of 200 mg/mL of sodium a-methyl hydrocinnamate, which is about 20% of the drug product composition. Based on the solubility data, it seems necessary for a syrup/elixir formulation to contain at least 20-40% co-solvents and/or complexing agents to keep the drug substance in solution at the formulation pH of 5-7 and also at gastric pH of 1.2.

ELIXIR® was thought to be a suitable formulation since it is observed to keep sodium α-methyl hydrocinnamate in solution at the target formulation strength of 200 mg/mL. Also, the use of alcohol (10-20%) in these preparations will eliminate the need for a second formulation preservative. Initially syrup and elixir formulations containing co-solvents but no cyclodextrin were prepared and compared for taste masking effect. The ELIXIR formulation was observed to have a sharp taste, hence it was eliminated from further studies with cyclodextrin.

Selection of Co-solvents and Complexing Agents

Different co-solvents such as alcohol, propylene glycol, polyethylene glycol 400, and glycerin, as well as complexing agents like cyclodextrin were evaluated during the preparation of elixir and syrup formulas. These co-solvents and complexing agents are used to keep the free α-methyl hydrocinnamic acid in solution at the target formulation pH as well as the gastric pH of about 1.2 to avoid precipitation of the free acid in stomach.

Alcohol, propylene glycol, polyethylene glycol 400, and glycerin have the potential to solubilize the API at formulation and gastric pH, however, cyclodextrin was observed to be more efficient at the gastric pH.

Two types of Cyclodextrin have been used in the formulation studies. Based on the physical appearance of the solutions and solubility data obtained at pH 1.2, the hydroxypropyl β cyclodextrin (Trappsol) was selected over the sulfo butyl ether β cyclodextrin (Captisol) for further studies. Cyclodextrins have been observed to be more efficient in keeping the free acid in solution at pH 1.2 than any other co-solvent evaluated. Another advantage of cyclodextrin is its potential to mask the bitter taste of the sodium salt.

Syrup formulations were prepared with and without Trappsol and compared for taste masking effect. The one containing 20% Trappsol was observed to mask the bitter taste to a significant extent and was selected as the final formulation.

Selection of Preservatives

Methylparaben at a concentration of 0.25% was selected as the suitable preservative for the syrup formulation in the pl-I range of 6-7. A preservative challenge test should be conducted at a later stage after the stability data of the formulation is available. The concentration of methylparaben may then be changed based on the results of the preservative challenge test.

Selection of Sweeteners

Syrup formulations were prepared using different combinations and percentages of the following sweeteners before selecting the final sweeteners and their concentrations: Sucrose syrup, High Fructose Corn syrup, Sodium saccharin, Aspartame, Acesulfame and Sucralose. The sweetener(s) was added to the formulation in addition to Trappsol.

Among the above, High Fructose Corn syrup was found to have a better taste-masking effect than Sucrose syrup. Sodium saccharin was found to impart greater initial sweetness than Aspartame but provided a very bitter after-taste. Acesulfame by itself provided a good initial sweetness with bitter after-taste but in combination with Sucralose provided a lingering sweet after-taste.

Based on the above observations a combination of 35% High Fructose Corn syrup, 1.25% Sucralose and 0.75% Acesulfame potassium were chosen for the final formulation in presence of 20% Trappsol.

Selection of Flavors.

A variety of flavors viz. Cherry, Grape, Lemon, Pineapple, Orange, Menthol, Chocolate, Mint, Chocolate mint were tried in syrup formulation containing High Fructose Corn syrup, Trappsol and Sodium saccharin. Based on the initial feedback from tasters for these formulations, the ones with orange flavor and chocolate flavor were selected for use in further formulation work using the final artificial sweetener i.e. Sucralose (1.25%) and Acesulfame potassium (0.75%) besides high fructose corn syrup and Trappsol. Formulation containing 8% Orange flavor was selected for the final development batch placed on stability.

Composition of Final Formulation

Studies carried out on the solubility of Sodium a-Methyl Hydrocinnamate and the flavor, sweetness and bioavailability of different formulations resulted in the selection of the following final formulation for carrying out accelerated stability testing:

| | |
|---|---|
| Sodium α-Methyl Hydrocinnamate | 20% w/v (16.7% w/w) |
| Methylparaben | 0.25% w/w |
| High Fructose Corn syrup | 35% w/w |
| Trappsol (hydroxypropyl β cyclodextrin) | 20% w/w |
| Sucralose | 1.25% w/w |
| Acesulfame potassium | 0.75% w/w |
| Orange flavor | 8.0% w/w |
| Coloring agent(FD&C Yellow # 6) | 0.03% w/w |
| Deionized Water | q.s. 100 mL |

Analytical Method and Development.

Method No. AM-038-R0 was developed to resolve the API Sodium α-Methyl Hydrocinnamate from its related compounds (known and unknown impurities) and the preservative Methylparaben. It is a stability indicating method and a draft version of this method has been used to analyze the formulation on stability. The initial and 15 day stability data is presented in Tables 5-8 herein.

Accelerated Stability Study

Formulation of α-Methyl Hydrocinnamate as an oral composition is described, and has been placed on room temperature and accelerated stability testing at storage conditions of 25° C./60% RH and 40° C./75% RH and was tested at the following time points: initial, 2 weeks, 1 month, 2 months, 3 months and 6 months. Stability data available up to this point of time is presented in the tables 5-8.

TABLE 5

Stability Data of Sodium α-Methyl Hydrocinnamate Syrup at 25° C./60% RH

| | Time point (n = 3) | |
|---|---|---|
| Test | Initial | 2 Weeks |
| Appearance: Color | Orange | Orange |
| Appearance: Clarity | Clear and viscous solution. | Clear and viscous solution. |
| pH | 7.8 | 7.9 |
| Assay: % Label Claim of NaAMHC | 106.3%; % RSD = 0.4 | 107.2%; % RSD = 0.3 |

TABLE 5-continued

Stability Data of Sodium α-Methyl Hydrocinnamate Syrup at 25° C./60% RH

| | Time point (n = 3) | |
|---|---|---|
| Test | Initial | 2 Weeks |
| % Total Related Compounds | 2.34%; % RSD = 1.3 | 1.85%; % RSD = 3.0 |
| Assay: % Label Claim of Methyl Paraben | 105.4%; % RSD = 0.5 | 106.0%; % RSD = 0.3 |

TABLE 6

Stability Data of placebo Syrup at 25° C./60% RH

| | Time point (n = 3) | |
|---|---|---|
| Test | Initial | 2 Weeks |
| Appearance: Color | Orange | Orange |
| Appearance: Clarity | Clear and viscous solution. | Clear and viscous solution. |
| pH | 3.5 | 3.5 |
| Assay: % Label Claim of NaAMHC | N/A | N/A |
| % Total Related Compounds | N/A | N/A |
| Assay: % Label Claim of Methyl Paraben | 104.7% | 104.7% |

TABLE 7

Stability Data of Sodium α-Methyl Hydrocinnamate Syrup at 40° C./75% RH

| | Time point (n = 3) | |
|---|---|---|
| Test | Initial | 2 Weeks |
| Appearance: Color | Orange | Orange |
| Appearance: Clarity | Clear and viscous solution. | Clear and viscous solution. |
| pH | 7.8 | 7.7 |
| Assay: % Label Claim of NaAMHC | 106.3%; % RSD = 0.4 | 107.2%; % RSD = 0.4 |
| % Total Related Compounds | 2.34%; % RSD = 1.3 | 3.22%; % RSD = 1.9 |
| Assay: % Label Claim of Methyl Paraben | 105.4%; % RSD = 0.5 | 104.6%; % RSD = 0.3 |

TABLE 8

Stability Data of Placebo Syrup at 40° C./75% RH

| | Time point (n = 1) | |
|---|---|---|
| Test | Initial | 2 Weeks |
| Appearance: Color | Orange | Orange |
| Appearance: Clarity | Clear and viscous solution. | Clear and viscous solution. |
| pH | 3.5 | 3.4 |
| Assay: % Label Claim of NaAMHC | N/A | N/A |
| % Total Related Compounds | N/A | N/A |
| Assay: % Label Claim of Methyl Paraben | 104.7% | 105.7% |

Based on the results obtained up to a 2 week period of the final formulation batch on stability, the inventors have demonstrated a final formulation provides acceptable taste masking properties and is stable at recommended storage condition.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

REFERENCES

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

Accordingly, the references are each incorporated herein in their entirety by reference.

What is claimed is:

1. A method for treating a subject, comprising administering to the subject an oral pharmaceutical formulation comprising:
    a. a pharmaceutically effective amount of an S isomer of α-methyl-hydrocinnamic acid, or a pharmaceutically acceptable salt thereof; and
    b. a pharmaceutically acceptable carrier or diluent,
        wherein the oral pharmaceutical formulation comprises less than 6% of the R isomer of α-methyl-hydrocinnamic acid and wherein the oral pharmaceutical composition is in solution or a dry solid,
            wherein the oral pharmaceutical formulation is administered to the subject by oral administration, and
            wherein the subject has been selected for administration of the oral pharmaceutical composition as one who will undergo a chemotherapeutic treatment or a radiation treatment or radiation exposure after the administration of the oral pharmaceutical formulation.

2. The method of claim 1, wherein the solution is as a dispersion, mixture, liquid, spray, or capsule.

3. The method of claim 1, wherein the dry solid is as a powder, pill, tablet, or capsule.

4. The method of claim 1, wherein the composition further comprises a flavoring agent.

5. The method of claim 1, wherein the pharmaceutically effective amount is 1 µg/kg of body weight to 150 mg/kg of body weight.

6. The method of claim 1, wherein said administering is everyday, every third day, every fourth day, every fifth day, every sixth day, or once a week prior to or up to the administration of the chemotherapeutic treatment or a radiation treatment or radiation exposure.

7. The method of claim 1, wherein administering is for a period of 1 week to 1 year prior to the administration of the chemotherapeutic treatment or a radiation treatment or radiation exposure.

8. The method of claim 1, wherein the radiation exposure is accidental radiation exposure.

9. The method of claim 1, wherein the subject has cancer.

10. A method for treating a subject prior to a transplantation, comprising administering to the subject an oral pharmaceutical formulation comprising:
   a. a pharmaceutically effective amount of an S isomer of α-methyl-hydrocinnamic acid, or a pharmaceutically acceptable salt thereof; and
   b. a pharmaceutically acceptable carrier or diluent,
   wherein the oral pharmaceutical formulation comprises less than 6% of the R isomer of α-methyl-hydrocinnamic acid and wherein the oral pharmaceutical composition is in solution or a dry solid, and
   wherein the oral pharmaceutical formulation is administered to the subject by oral administration, and
   wherein the subject has been selected for administration of the oral pharmaceutical composition as a recipient of an organ transplant after the administration of the oral pharmaceutical formulation.

11. The method of claim 10, wherein the solution is as a dispersion, mixture, liquid, spray, or capsule.

12. The method of claim 10, wherein the dry solid as a powder, pill, tablet, or capsule.

13. The method of claim 10, wherein the composition further comprises a flavoring agent.

14. The method of claim 10, wherein the pharmaceutically effective amount is 1 μg/kg of body weight to 150 mg/kg of body weight.

15. The method of claim 10, wherein said administering is everyday, every third day, every fourth day, every fifth day, every sixth day, or once a week prior to or up to the transplantation.

16. The method of claim 10, wherein administering is for a period of 1 week to 1 year prior to the transplantation.

* * * * *